(12) United States Patent
Allegretti et al.

(10) Patent No.: US 7,705,050 B2
(45) Date of Patent: Apr. 27, 2010

(54) AMIDES, USEFUL IN THE INHIBITION OF IL-8-INDUCED CHEMOTAXIS OF NEUTROPHILS

(76) Inventors: Marcello Allegretti, c/o Dompé S.p.A., Via Campo di Pile, I-67100 L'Aquila AQ (IT); Riccardo Bertini, c/o Dompé S.p.A., Via Campo di Pile, I-67100 L'Aquila AQ (IT); Cinzia Bizzarri, c/o Dompé S.p.A., Via Campo di Pile, I-67100 L'Aquila AQ (IT); Vilma Sabbatini, c/o Dompé S.p.A., Via Campo di Pile, I-67100 L'Aquila AQ (IT); Ginfranco Caselli, c/o Dompé S.p.A., Via Campo di Pile, I-67100 L'Aquila AQ (IT); Maria Candida Cesta, c/o Dompé S.p.A., Via Campo di Pile, I-67100 L'Aquila AQ (IT); Carmelo Gandolfi, L'Aquila (IT); Janete Peloia Barroso Gandolfi, legal representative, Via Dolci 1, Milan (IT); Giulio Agostino Gandolfi, legal representative, Via P. Mante Gazia 25/9, 20156 Milano (IT); Maria Carla Gandolfi, legal representative, Via Dolci 1, Milan (IT); Arrigo Aldo Gandolfi, legal representative, Via Freina 100, 21097 Saronno (IT); Francesco Colotta, c/o Dompé S.p.A., Via Campo di Pile, I-67100 L'Aquila AQ (IT)

( * ) Notice: Subject to any disclaimer, the term of this patent is extended or adjusted under 35 U.S.C. 154(b) by 336 days.

(21) Appl. No.: 10/203,463

(22) PCT Filed: Feb. 6, 2001

(86) PCT No.: PCT/EP01/01285

§ 371 (c)(1),
(2), (4) Date: Oct. 27, 2003

(87) PCT Pub. No.: WO01/58852

PCT Pub. Date: Aug. 16, 2001

(65) Prior Publication Data
US 2004/0181073 A1    Sep. 16, 2004

(30) Foreign Application Priority Data
Feb. 11, 2000    (IT)    .......................... MI2000A0227

(51) Int. Cl.
A61K 37/44    (2006.01)

(52) U.S. Cl. ...................................... 514/561; 514/567

(58) Field of Classification Search .................. 562/444, 562/445, 450; 514/561, 567
See application file for complete search history.

(56) References Cited

FOREIGN PATENT DOCUMENTS

| EP | 0 305 089 A | 3/1989 |
|---|---|---|
| EP | 0 618 223 A | 10/1994 |
| WO | 94/03209 * | 2/1994 |
| WO | 99 24416 A | 5/1999 |
| WO | 99 36393 A | 7/1999 |
| WO | 00 02903 A | 1/2000 |
| WO | 00 26202 A | 5/2000 |

OTHER PUBLICATIONS

Kwapiszewski et al, Acta Poloniae Pharmaceutica, vol. 42(6), 1985, 545-549.*
Miranda et al., J. Am. Chem. Soc., vol. 121, No. 49, pp. 11569-11570 (1999).
Levit et al., Russ. J. Org. Chem., vol. 34, No. 3, pp. 346-350 (1998).
Helmchen et al., Tetrahedron Lett., No. 16, pp. 1417-1420 (1977).
Herlinger et al., Justus Liebigs Ann. Chem., vol. 706, pp. 37-46 (1967).

* cited by examiner

*Primary Examiner*—Shailendra Kumar
(74) *Attorney, Agent, or Firm*—Birch, Stewart, Kolasch & Birch, LLP

(57) ABSTRACT

N-(2-aryl-propionyl)-amides of formula (I) are described.

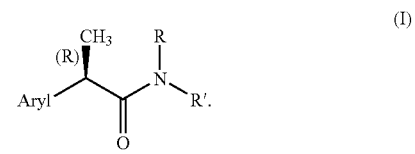

The process for their preparation and pharmaceutical preparations thereof are also described.

The amides of the invention are useful in the prevention and treatment of tissue damage due to the exacerbate recruitment of polymorphonuclear neutrophils (leukocytes PMN) at the inflammatory sites. In particular, the invention relates to the R enantiomers of N-(2-aryl-propionyl)amides of formula (I) for use in the inhibition of the chemotaxis of neutrophils induced by IL-8. The compounds of the invention are used in the treatment of psoriasis, ulcerative cholitis, glomerular nephritis, acute respiratory insufficiency, idiopathic fibrosis, and rheumatoid arthritis.

16 Claims, No Drawings

AMIDES, USEFUL IN THE INHIBITION OF IL-8-INDUCED CHEMOTAXIS OF NEUTROPHILS

This application is the national phase under 35 U.S.C. §371 of PCT International Application No. PCT/EP01/01285 which has an International filing date of Feb. 6, 2001, which designated the United States of America.

FIELD OF THE INVENTION

The present invention relates to N-(2-aryl-propionyl)-amides, the process for their preparation and the pharmaceutical preparations thereof useful in the prevention and treatment of tissue damage due to the exacerbate recruitment of polymorphonuclear neutrophils (leukocytes PMN) at the inflammatory sites. In particular, the invention relates to the R enantiomers of N-(2-aryl-propionyl)amides for use in the inhibition of the chemotaxis of neutrophils induced by IL-8.

BACKGROUND OF THE INVENTION

Chemokines constitute a family of cytokines of low molecular weight directly involved in inflammatory response, in the displacements of immune cells and in the directional migration of cellular elements. The term "chemokines", which is a contraction of the words chemotactic cytokines, highlights the typical biological function of these cell mediators.

Chemokines are divided into two subspecies which differ according to the sequences of amino acids CC and CXC containing the two cysteine residues, invariably present in the N-terminal portion of the protein. In one case, for example in the case of monocyte chemoattractant protein-1 (MCP-1), the two cysteine residues are contiguous, in the other case, for example in the case of interleukin-8 (IL-8) and certain of its closest affines (GRO-$\alpha$,$\beta$,$\gamma$, ENA-78, NAP-2, GCP-2), a second amino acid is interspaced between the two cysteines.

From the functional standpoint, chemokines are distinguished from the other cytokines by the cellular specificity of their action: each of them regulates in a specific way the migration and the functionality of a single cell species. Thus, if MCP-1 influences and directs the movements of monocytes, IL-8 performs the pre-eminent role of specific neutrophil-chemoattractant factor. Confirmation thereof is provided by the presence of high concentrations of IL-8 in the inflammatory sites and in the surrounding fluids, ascertained during the course of many acute illnesses mediated by neutrophils, as well as the prevention of the severity of tissue damage and reduced infiltration of neutrophils observed after administration of anti-IL-8 antibodies in the course of experiments conducted on animal models representing neutrophil-dependent illnesses. Typical clinical situations are the damage caused by cerebral re-perfusion and the damage caused by ischaemia and re-perfusion of the myocardium.

These observations have corroborated the hypothesis that IL-8 constitutes the principal mediator of tissue damage induced by neutrophils, so much so as to cause interleukin-8 to be proposed as optimal target for therapeutic interventions aimed at resolving acute inflammatory states mediated by neutrophils (N. Mukaida et al., Inflammation Research 47 (Suppl. 3) S151, 1998). For this purpose, as an alternative to the use of anti-IL-8 antibodies, substances of low molecular weight could be of great interest and of clinical usefulness, which, by inserting themselves in the inter-cellular and intra-cellular circuits of transmission of the signal, may be able to inhibit the migration of human neutrophils stimulated by IL-8 and by its affines in a highly specific way.

Recently PCT/EP/9907740 disclosed N-acylsulphonamides of (R)-2-arylpropionic acids having inhibitory activity on the chemotaxis of neutrophils stimulated by IL-8 irrespective of the inflammatory processes linked to inhibition of cyclo-oxygenase (COX-1 and/or COX-2).

On the other hand, the inhibition of the synthesis of prostaglandins (PGs) peculiar to the (S) enantiomers of 2-aryl-propionic acids and of certain of their derivatives would appear to have a negative effect on the dynamics, of the neutrophil-dependent inflammatory process stimulated by IL-8, such as to exacerbate the illness itself. In these circumstances, with the inhibition of PG synthesis, the endogenous factor, $PGE_2$, which controls the synthesis of Tumour Necrosis Factor-alpha (TNF-$\alpha$), comes to be missing. Consequently, in competition with IL-8 itself, TNF-$\alpha$ may contribute, together with the cytokines IL-6 and IL-1 and with the molecules of the adhesion (E-selectin, ICAM-1 and C-reactive protein) to exacerbating the degree and severity of the tissue damage in the course of acute myocardial infarction (R. Pudil et al., Clin. Chim. Acta, 280, 127, 1999).

Also the known (R)-2-(4-isobutyl-phenyl)-propionamide (PCT/EP/9907740) has proved active in the prevention and inhibition of chemotaxis of human leucocytes induced by IL-8, a property instead altogether absent in the (S) enantiomer (Table 1).

TABLE 1

| Compound | % inhibition of chemotaxis of human PMNs stimulated by IL-8 (10 ng/mL) |
|---|---|
| (R)-2-(4-isobutyl-phenyl)-propionamide* | 57 ± 12 |
| (S)-2-(4-isobutyl-phenyl)-propionamide* | −2 ± 8 |

*conc. $10^{-8}$ M

In addition, the same compound and the corresponding (R)—N-methyl-2-(4-isobutyl phenyl)-propionamide, albeit less potent [25±9% inhibition at a concentration of $10^{-8}$ M] as inhibitor of leucocyte chemotaxis stimulated by IL-8 (10 ng/mL), are characterized in that they down-regulate the production of TNF-$\alpha$ (stimulated in murine macrophages by $H_2O_2$ and by liposaccharides), as well as in that they do not inhibit the synthesis of $PGE_2$ in the macrophages after stimulation with lipopolysaccharides (LPSs) at 1 µg/mL. Instead, in the same experimental conditions, S-ketoprofen (taken as a typical example of (S) enantiomer of 2-aryl-propionic acids, COX inhibitors), stimulates in macrophages the amplification of TNF-$\alpha$ synthesis induced by LPSs with a percent variation of 300% for the synthesis and release of TNF-$\alpha$; in fact, in the presence of control values of the cytokine present in the incubation medium alone of less than the detectable minimum (20 pg/mL), values of 10±5 ng/mL are found in the presence of LPSs, whereas values of 39±5 ng/mL are found in the presence of LPSs and of S-ketoprofen $10^{-5}$ M. (Ghezzi et al., J. Pharmacol. Exp. Therap., 287, 969-974, 1998). More recently, it has been shown that this sensible increase in TNF-$\alpha$ release is a direct consequence of the stimulation of TNF-$\alpha$-mRNA by S-ketoprofen (P. Mascagni et al., Eur. Cytokine Netw., 11:185-192,2000).

Amides of 2-arylpropionic acids with amino alcohols are described in ES 500990 and in ES 2007236 for the preparation of N-($\alpha$-hydroxyethyl)-d,1-2-(4 isobutyl)propionamides.

Also known are amides of ibuprofen with L and D, L-amino acids (W. Kwapiszewski et al., Acta Pol. Pharm., 42, 545, 1985), and more generally amides of racemates and of S-enantiomers of 2-aryl-propionic acids with glycine (P. Singh et al., Indian J. Chem., sect. B, 29B, 551, 1990) and with the following amino acids: lysine, glutamic acid, and aspartic acid [A. Reiner, U.S. Pat. No. 4,341,798].

More frequently, these compounds have been evaluated as mixtures of diastereoisomers without it being possible to define the contribution of the individual diastereoisomers.

Amides of enantiomers of 2-arylpropionic acids with taurine, glutamine, ornithine, arginine, glutamic acid, aspartic acid, serine, and alanine are known as urinary metabolites of these acids in various animal species (R. I. Jeffrey et al., Xenobiotica, 4, 253, 1978, and references cited therein).

Other amides, studied as pro-drugs of 2-arylpropionic acids, have been described by S. Biniecki et al., PL 114050, H. A. Kguen et al., Arzneim-Forsh., 46, 891, 1986 and G. L. Levitt et al., Russ. J. Org. Chem., 34, 346, 1998. Such amides are credited with quite a good anti-inflammatory activity associated to reduced side effects and good tolerability at the gastro-intestinal level that are believed to compensate for the loss of potency observed in comparison with their precursors.

The loss of every residual fibrinolytic activity has been described for (±)-ibuprofen and other non-steroidal anti-inflammatory agents, such as Indomethacin, flufenamic acid and mefenamic acid after conversion into the corresponding amides with 2-aminomethyl-pyridine (G. Orzalesi et al., Progress in Fibrinolysis and Thrombolysis, 3, 483, 1978).

In a comparative study, the anti-inflammatory, analgesic and antipyretic properties, the behavioural effects and acute toxicity in the mouse were evaluated for a series of amides of ibuprofen, of ketoprofen (both as racemates), and of 3-benzoylphenylacetic acid (R. C. W. Spickett et al., Eur. J. Med. Chem. Chim. Ther., Nov. 7, 1976). The comparison associates to the simple amides (—CONH2) and their N-ethyl and N-dimethyl derivatives, the corresponding ureides and thioureides, as well as the anilides and certain heterocyclic amides, such as those with 2-aminothiazolidine, 2-aminothiazole, 2-amino-4-methyl-pyridine and 1-phenyl-2,3-dimethyl-4-amino-pyrazole. The pharmacological study has led to the selection and development of (R,S)-2-[3-benzoylphenylpropionamido]-4-methyl-pyridine, also known by the name of Pirketoprofen [A. Gallardo, G B 1436502].

Moreover the use of R-2-arylpropionic acids as drugs for the treatment of colorectal tumours and cystic fibrosis has been recently described (U.S. Pat. No. 5,955,504 and U.S. Pat. No. 5,981,592).

DESCRIPTION OF THE INVENTION

It has now been found that amides structurally linked to (R)-2-(4-isobutyl-phenyl)-propionamide, characterized by appropriate substituents, show surprising properties of inhibition of chemotaxis induced by IL-8.

Examples of such substituents are residues of an α-amino acid selected in the group consisting in glycine, L-alanine, D-alanine and L-serine, groups of formula —$CH_2$—$CH_2$—OH, $CH_2$—$CH_2$O—$CH_2$—$CH_2$OH or aromatic or heteroaromatic radicals, such as phenyl and pyridyl.

The compounds are obtained by reaction (in the presence of a convenient base) of the chloride of (R)-2-(4-isobutylphenyl)propionic acid with an appropriate amine and with the methyl esters of the α-amino acids previously indicated.

In the latter case, the subsequent saponification of the carboxyesters, in non-racemizing conditions, has enabled to obtain the free acids of the individual amides.

The amides of the invention, as such or after salification, have good characteristics of solubility.

The properties of inhibition of chemotaxis induced by IL-8 have proven surprisingly dependent upon the stereochemistry and upon the steric, electronic and polar effects of the substituents on the amidic nitrogen. It has in fact been noted, for example, that amides with amino acids of the L series are more active than amides with amino acids of the D series. Again, in the case of aromatic or hetero-aromatic amides, the presence of substituents on the aromatic ring strongly influences the activity. Also the polar interactions of an intramolecular type, for example intramolecular hydrogen bonds, have at times proven critical for pharmacological activity.

DETAILED DESCRIPTION OF THE INVENTION

The following paragraphs provide definitions of outstanding chemical moieties that make up the compounds according to the invention and are intended to apply uniformly throughout the specification and claims unless an otherwise expressly set out definition provides a broader definition.

"$C_1$-$C_4$-alkyl" or "$C_1$-$C_5$-alkyl" or "$C_1$-$C_6$-alkyl" refer to monovalent alkyl groups having 1 to 4 or 1 to 5 or 1 to 6 carbon atoms. These terms are exemplified by groups such as methyl, ethyl, n-propyl, isopropyl, n-butyl, isobutyl, tert-butyl, and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, biphenyl, naphthyl, phenantrenyl and the like.

"Alkenyl" refers to alkenyl groups preferably having from 2 to 5 carbon atoms and having one or more sites of alkenyl unsaturation. Preferred alkenyl groups include ethenyl (—CH═$CH_2$), n-2-propenyl(allyl, —$CH_2$CH═$CH_2$) and the like.

"Substituted or unsubstituted": unless otherwise constrained by the definition of the individual substituent, the above set out groups, like "alkyl", "alkenyl", "aryl" groups etc. can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", primary, secondary or tertiary amino groups or quarternary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides or cycloalkanes, but also acetals, thioacetals, aminals formed by ring closure for instance in an effort to obtain a protective group.

"Pharmaceutically acceptable salts" refers to salts or complexes of the below-identified compounds of formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art. Examples of salts also include acid addition salts formed with inorganic bases such as sodium hydroxyde and with organic bases such as tromethamine, L-lysine, L-arginine and the like.

The present invention relates to amides of the R enantiomers of 2-aryl-propionic acids of formula (I)

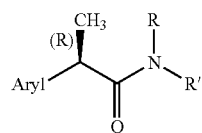

(I)

and pharmaceutically acceptable salts thereof, wherein:

Aryl is a substituted or unsubstituted aryl group;

R represents H, $C_1$-$C_4$-alkyl, allyl, propargyl, $CH_2$—$CO_2H$ or $(CH_2)_2$—$CO_2H$;

R' is:
an amino acid residue consisting of straight or branched $C_1$-$C_6$-alkyl, alkenyl, cycloalkyl, phenylalkyl substituted with one or more carboxy group $CO_2H$;
an amino acid residue consisting of straight or branched $C_1$-$C_6$-alkyl, alkenyl, cycloalkyl, phenylalkyl substituted with one or more carboxy group $CO_2H$ and with a heteroatom selected from oxygen or sulphur;
a residue of formula —$CH_2$—$CH_2X$—$(CH_2$—$CH_2O)_nR$ wherein R is hereinbefore defined; n being an integer from 0 to 5, whilst X is oxygen or sulphur;
a residue of formula (R) or (S)—$CH(CH_3)$—$CH_2$—O—$CH_2$—$CH_2$—OH;
a residue of formula OR, wherein R is hereinbefore defined;
a residue of formula (III)

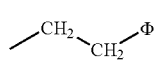

(III)

wherein Φ represents 2-(1-methyl-pyrrolidyl), 2-pyridyl, 4-pyridyl, 1-imidazolyl, 4-imidazolyl, 1-methyl-4-imidazolyl, 1-methyl-5-imidazolyl or a NRaRb group wherein each Ra and Rb, which may be the same or different, represent $C_1$-$C_6$ alkyl or —$(CH_2)_m$—OH hydroxyalkyl wherein m is an integer from 2 to 3, and, alternatively, Ra and Rb together with the atom of N to which they are bound, constitute a heterocycle from 3 to 7 members of formula (IV)

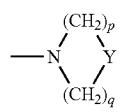

(IV)

wherein
Y represents a single bond, $CH_2$, O, S or N-Rc, Rc being H, $C_1$-$C_6$ alkyl, $(CH_2)_m$—OH hydroxyalkyl, a —$(CH_2)_{m'}$—Ar' residue wherein Ar' is an aryl, heteroaryl, cycloaliphatic and/or heterocycloaliphatic residue, m' is zero or an integer from 1 to 3, p and q, each independently, is an integer from 1 to 3 a heteroaryl selected in the group consisting in 2-pyridyl or 4-pyridyl, 2-pyrimidinyl or 4-pyrimidinyl; 2-pyrazinyl, 5-methyl-2-pyrazinyl; 3-1,2,4-thiazinyl; 3-1,2,4-thiazolyl, 3-1-benzyl-1,2,4-thiazolyl; 2-1,3-thiazolidinyl, 2-1,3-thiazolyl, 1,3-oxazolyl, 3-isoxazolyl, 4-dihydro-3-oxo-isoxazolyl, 5-methyl-isoxazol-4-yl, 2-imidazolyl, 4-imidazolyl-5-carboxyamide and 2-imidazolyl-4,5-dicarbonitrile, 5-indanyl, 5-indazolyl, 7-aza-indol-3-yl, 2- or 3- or 4-quinolinyl; for use as agents inhibiting the chemotaxis of neutrophils induced by interleukin-8.

The present invention further relates to novel (R) enantiomers of 2-aryl-propionic amides of formula (Ia)

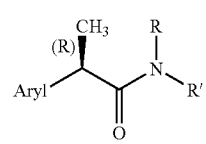

(Ia)

and pharmaceutically acceptable salts thereof, wherein:

Aryl represents a phenyl group substituted with a group selected from isopropyl, acetyl, (2",6"-dichlorophenyl) amino, α-hydroxyisopropyl, (R,S) α-hydroxyethyl and its single R and S isomers, (R,S)-α-hydroxybenzyl and its single R and S isomers, and (R,S)—(α-methylbenzyl) and its single R and S isomers; (R,S)-α-hydroxy-α-methylbenzyl and its single R and S isomers;

R represents H, $C_1$-$C_4$-alkyl, allyl, propargyl, $CH_2$—$CO_2H$ or $(CH_2)_2$—$CO_2H$;

R' is:
an amino acid residue consisting of straight or branched $C_1$-$C_6$-alkyl, alkenyl, cycloalkyl, phenylalkyl substituted with one or more carboxy group $CO_2H$;
an amino acid residue consisting of straight or branched $C_1$-$C_6$-alkyl, alkenyl, cycloalkyl, phenylalkyl substituted with one or more carboxy group $CO_2H$ and with a heteroatom selected from oxygen or sulphur;
a residue of formula —$CH_2$—$CH_2X$—$(CH_2$—$CH_2O)_nR$ wherein R is hereinbefore defined; n being an integer from 0 to 5, whilst X is oxygen or sulphur;
a residue of formula (R) or (S)—$CH(CH_3)$—$CH_2$—O—$CH_2$—$CH_2$—OH;
a residue of formula OR, wherein R is hereinbefore defined;
a residue of formula (III)

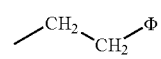

(III)

wherein

Φ represents 2-(1-methyl-pyrrolidyl), 2-pyridyl, 4-pyridyl, 1-imidazolyl, 4-imidazolyl, 1-methyl-4-imidazolyl, 1-methyl-5-imidazolyl or a NRaRb group wherein each Ra and Rb, which may be the same or different, represent $C_1$-$C_5$ alkyl or —$(CH_2)_m$—OH hydroxyalkyl wherein m is an integer from 2 to 3, and, alternatively, Ra and Rb together with the atom of N to which they are bound, constitute a heterocycle from 3 to 7 members of formula (IV)

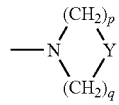
(IV)

wherein
Y represents a single bond, $CH_2$, O, S or N-Rc, Rc being H, $C_1$-$C_5$ alkyl, $(CH_2)_m$—OH hydroxyalkyl, a —$(CH_2)_{m'}$— Ar' residue where Ar' is an aryl, aromatic heteroaryl, cycloaliphatic and/or heterocycloaliphatic residue, m' is zero or an integer from 1 to 3, each p and q, independently of one another, is an integer from 1 to 3;
a heteroaryl selected in the group consisting in 2-pyridyl or 4-pyridyl, 2-pyrimidinyl or 4-pyrimidinyl; 2-pyrazinyl, 5-methyl-2-pyrazinyl; 3-1,2,4-thiazinyl; 3-1,2,4-thiazolyl, 3-1-benzyl-1,2,4-thiazolyl; 2-1,3-thiazolidinyl, 2-1,3-thiazolyl, 1,3-oxazolyl, 3-isoxazolyl, 4-dihydro-3-oxo-isoxazolyl, 5-methyl-isoxazol-4-yl, 2-imidazolyl, 4-imidazolyl-5-carboxyamide and 2-imidazolyl-4,5-dicarbonitrile, 5-indanyl, 5-indazolyl, 7-aza-indol-3-yl, 2- or 3- or 4-quinolinyl.

Examples of the Ar' aryl residue are phenyl, diphenylmethyl, 4,4'-difluoro-diphenylmethyl; examples of heteroaryl aromatic residues are pyridyl, imidazolyl; examples of cycloaliphatic or heterocycloaliphatic residues are cyclohexyl, cyclopentyl, 4-morpholyl and 1-piperidyl.

The invention further relates to the compounds defined hereinbefore for use as medicaments.

The term "aryl group" preferably means phenyl optionally substituted with one to three substituents, which are the same or different, selected from halogen atoms, $C_1$-$C_4$ alkyl, $C_1$-$C_4$ alkoxy, hydroxy, $C_1$-$C_7$ acyloxy, cyano, nitro, amino, $C_1$-$C_3$ acylamino, halo $C_1$-$C_3$ alkyl, hydroxy $C_1$-$C_3$ alkyl, halo $C_1$-$C_3$ alkoxy, hydroxy $C_1$-$C_3$ arylalkyl, benzoyl or the known moiety of known antiinflammatory 2-arylpropionic acids such as ibuprofen, ketoprofen, suprofen, pirprofen, fenoprofen. The aryl group is more preferably selected in the group consisting in phenyl, 4-methyl-phenyl, 3-isopropyl-phenyl, 4-methoxy-phenyl, 4-acetoxy-phenyl, 4-benzoyloxyphenyl, 4-hydroxyphenyl, 4-isobutylphenyl, 4-(2,2-dimethyl)vinylphenyl, $(CH_3)_2C=CH-C_6H_4-$, 4-(2-methyl)-allyl-phenyl, 3-benzoyl-phenyl, 3-phenoxy-phenyl, 3-benzyl-phenyl, 3-$C_6H_5$—CH(OH)-phenyl, 5-benzoyl-thien-2-yl, 4-thienoyl-phenyl, 1-oxo-2-isoindolinyl-phenyl, 2-fluoro-4-biphenylyl, 6-methoxynaphthyl, 5-benzoyl-2-acetoxy-phenyl, 5-benzoyl-2-hydroxy-phenyl, 3-α-methylbenzyl-phenyl, 3-hydroxypropyl-phenyl, 3-hydroxyethyl-phenyl.

The amino acid residue R' as hereinbefore defined is preferably a residue of an L-α-amino acid and more preferably is selected in the group consisting of Leanne, valine, leucine, isoleucine, nor-leucine, phenylalanine, tyrosine, histidine, S-methylcysteine, S-carboxymethylcysteine, S-2-hydroxyethylcysteine, methionine, O-methylserine, O-2-hydroxyethylserine, proline, hydroxyproline, glutamic acid, aspartic acid, glutamine or a residue of glycine, phenylglycine, β-alanine, γ-amino-butyric acid, δ-amino-valeric acid, cis-4-amino-cyclohexanecarboxylic acid, trans-4-aminomethyl-cyclohexanecarboxylic acid, 3-amino-1,5-pentandioic acid or a residue of formula (II)

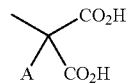
(II)

wherein the A substituent represents H, straight or branched $C_1$-$C_6$-alkyl, $(CH_2)_{n_i}CO_2H$ where $n_i$ is an integer between 1 and 3, benzyl, p-hydroxy-benzyl, —$CH_2$—O—$C_2H_5$, —$CH_2$—S—$CH_3$, $CH_2$—S—$CH_2$—$CO_2H$, the residues of the acids indicated above being in the form of free acids or of salts as specified hereinafter or in the form of methyl, ethyl and allyl esters thereof.

Also salts of the compounds of formula (I) with pharmaceutically acceptable bases or acids are another object of the present invention.

In the compounds of formula (I), R is more preferably hydrogen and R' is the residue of an amino acid, such as glycine, cis-4-cyclohexanecarboxylic acid, aminomalonic acid, aminomethyl-malonic acid, benzyl-aminomalonic acid, or the residue of a monocarboxylic or bicarboxylic L-α-amino acid, or again the residue of a dipeptide selected in the group consisting in L-alanylglycine, glycyl-L-alanine and glycyl-D-alanine.

More particularly preferred are the compounds of formula (I) wherein R is hydrogen and R' is the residue of L-alanine, L-carboxymethylcysteine, L-phenylalanine, L-leucine, L-methionine, L-O-methylserine, L-alanyl-glycine.

Particularly preferred amides of formula (I) are those wherein R is hydrogen and R' is the hereinbefore defined group —$CH_2$—$CH_2$—O—(—$CH_2$—$CH_2$—O)$_n$—R, n is an integer from 0 to 2, more preferably the integer 1.

Preferred amides of formula (I) are also those wherein R is hydrogen and R' is a substituent of formula (III)

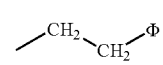
(III)

wherein Φ is an —NRaRb basic residue, such as N,N-dimethyl amine, N,N-diethyl amine, N,N-diisopropyl amine, 4-morpholyl, 1-piperidyl, 1-pyrrolidyl, 1-piperazinyl, 1-(4-benzyl)-piperazinyl, 1-(4-diphenyl-methyl)-piperazinyl, 1-(4-(4',4''-difluoro-diphenyl)-methyl)-piperazinyl, 1-(4-ethyl)-piperazinyl, 1-(4-hydroxyethyl)-piperazinyl.

Particularly preferred monosubstituted amides of formula (I) are those wherein the heteroaryl group R' is 2- or 4-pyridyl, 2- and 4-pyrimidinyl, 2-pyrazinyl, 2-1,3-thiazolyl, 1-1,3-thiazolidinyl and 2-imidazolidyl, and more preferably 4-pyridyl.

Specific examples of the compounds of the invention are:

(R)(−)-2-(4'-isobutyl-phenyl)-N-methyl propionamide;

(R)(−)-2-[(4'-isobutyl)phenyl]-N-carboxymethyl propionamide;

(R)(−)-2-[(4'-isobutyl)phenyl]-N-methoxycarbonylmethyl propionamide;

cis-(R)-2-[(4'-isobutyl)phenyl]-N-(4'carboxy-cyclohexyl) propionamide;

trans-(R)-2-[(4'-isobutyl)phenyl]-N-(4'carboxymethyl-cyclohexyl)propionamide;

(R,S')-2-[(4'-isobutyl)phenyl]-N-(2-methoxycarbonylethyl) propionamide;

(R,S')-2-[(4'-isobutyl)phenyl]-N-(2-carboxyethyl)propionamide;

(R,S')-2-[(4'-methoxy)phenyl]-N-(2-carboxyethyl)propionamide;

(R)—N-[2'-(4"-isobutylphenyl)propanoyl]-2-amino acrylic acid and its methyl ester;

(R)(−)-2-[(4'-isobutyl)phenyl]-N-(2"-hydroxyethoxyethyl) propionamide;

(R,S')-2-[(4"-isobutyl)phenyl]-N-[1'-methyl-2'-(2"-hydroxyethoxy)ethyl]propionamide;

(R,R')-2-[(4"-isobutyl)phenyl]-N-[1'-methyl-2'-(2"-hydroxyethoxy)ethyl]propionamide;

(R)(−)-2-(4'-isobutyl-phenyl)-N-(2"-pyridyl)propionamide and its hydrochloride;

(R)(−)-2-(4'-isobutyl-phenyl)-N-(4"-pyridyl)propionamide and its hydrochloride;

(R)(−)-2-[(3'-benzoyl)phenyl]-N-(2"-pyridyl)propionamide and its hydrochloride;

(R)(−)-2-[(2'-hydroxy-5'-benzoyl)phenyl]-N-(2"-pyridyl) propionamide and its hydrochloride;

(R)(−)-2-[(2'-hydroxy-5'-benzoyl)phenyl]-N-(4"-pyridyl) propionamide and its hydrochloride;

(R)(−)-2-[(2'-hydroxy-5'-benzoyl)phenyl]-N-carboxymethyl propionamide;

(R)(−)-2-(4'-isobutyl-phenyl)-N-(2"-pyrazinyl)propionamide and its hydrochloride;

(R)(−)-2-(4'-isobutyl-phenyl)-N-(2"-pyrimidinyl)propionamide and its hydrochloride;

5)(−)-2-(4'-isobutyl-phenyl)-N-(4"-pyrimidinyl)propionamide and its hydrochloride;

(R)(−)-2-[(3'-isopropyl)phenyl]-N-carboxymethyl propionamide;

(R,S')(−)-2-[(3'-α-methylbenzyl)phenyl]-N-carboxymethyl propionamide;

(R,R')(−)-2-[(3'-α-methylbenzyl)phenyl]-N-carboxymethyl propionamide;

For the preparation of the amides of the invention of formula (I) known methods are used, which consist in reacting an appropriately activated form of an R-2-arylpropionic acid of formula (V) with an amine of formula (VI) in non-racemizing reaction conditions in the presence, if so desired, of a molar excess of a base:

(V)

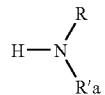

(VI)

wherein AT in the compounds of formula (V) is the residue activating the carboxy group.

Examples of activated forms of 2-arylpropionic acids of formula (V) with AT=H are the corresponding chlorides (AT=Cl), the imidazolides (AT=1-imidazole), esters with phenols such as p-nitrophenol (AT=pNO$_2$—C$_6$H$_4$O) or activated forms obtained by reaction in the presence of 1-hydroxybenzotriazole (HOBT) or of a carbodiimide, such as dicyclohexylcarbodiimide.

The amines of formula (VI) are primary or secondary amines wherein R is as defined above and R'a represents:

the residue of an ester of an L-α-amino acid selected in the group consisting in alanine, valine, leucine, isoleucine, nor-leucine, phenylalanine, tyrosine, histidine, S-methylcysteine, S-carboxymethylcysteine, S-2-hydroxyethylcysteine, methyonine, O-methylserine, O-2-hydroxyethyl-serine, proline, hydroxyproline;

the residue of an ester of glycine, phenylglycine, β-alanine, γ-amino-butyric acid, δ-amino-valeric acid, cis-4-amino-cyclohexanecarboxylic acid, trans-4-aminomethyl-cyclohexanecarboxylic acid, 3-amino-1,5-pentanedioic acid;

a residue of a malonic acid of formula (II')

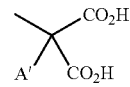

(II')

wherein the substituent A' is H, straight or branched C$_1$-C$_5$-alkyl, —(CH$_2$)$_{ni}$CO$_2$ methyl and/or ethyl ester, where ni is an integer between 1 and 3, benzyl, p-hydroxybenzyl, —CH$_2$—O—C$_2$H$_5$, —CH$_2$—S—CH$_3$ and —CH$_2$—S—CH$_2$—CO$_2$ methyl ester and/or ethyl ester;

a residue of formula —CH$_2$—CH$_2$X—(CH$_2$—CH$_2$O)$_n$R wherein R is as defined previously, or a residue of formula (R) or (S)—CH(CH$_3$)CH$_2$—O—CH$_2$—CH$_2$—OH;

a residue of formula (III)

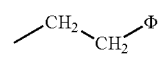

(III)

wherein Φ is as defined previously;
heteroaryl as defined previously.

The formation of the amides of formula (I) by reaction of an activated form of an acid of formula (V) with a secondary or primary amine of formula (VI) is usually carried out at room temperature, using conventional protic or aprotic solvents, preferably dehydrated on molecular sieves, or their mixtures. Said solvents comprise esters such as ethyl acetate, methyl acetate, and ethyl formiate, nitriles such as acetonitrile, straight or cyclic ethers such as dioxane, tetrahydrofuran, ethyl ether, and sulpholane, amides such as dimethylformamide and formamide, halogenated solvents such as dichloromethane, aromatic hydrocarbons such as toluene and chlorobenzene, or hetero-aromatic hydrocarbons such as pyridine and picoline.

The reactions may be carried out in the presence of a base; preferred inorganic bases are alkaline and alkaline-earth carbonates and bicarbonates, such as finely ground potassium carbonate, potassium bicarbonate and magnesium carbonate or calcium carbonate.

A product of formula (Ia), thus obtained:

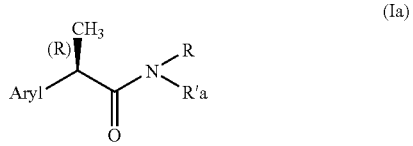

(Ia)

wherein aryl, R and R'a have the meanings previously described, as any compound of formula (I), if so desired, may be converted into another product of formula (I) by means of release of any protective groups that might be present in the compounds of formula (Ia) and/or by selective hydrolysis of ester groups. A particularly preferred ester group, alongside the usual methyl and ethyl groups, is the allyl group, which is removable in highly selective and non-racemizing conditions, for example by transferring the allyl group to the morpholine, which, in the presence of Pd(0) as catalyst, acts as transferor of hydrogen and as nucleophil acceptor in accordance with the procedure described in J. Org. Chem., 54, 751 (1989). If so desired, a compound of formula (Ia), wherein R'a is the residue of an α-amino acid β-substituted by free or etherified thiol groups or by a hydroxy free or esterified by an aliphatic acid or with a sulphonic (methane sulphonic, benzene sulphonic, p-toluene sulphonic) acid, may be subjected to β-elimination of said substituents so as to obtain, by treatment with an excess of $BBr_3$, compounds of formula (I) wherein R' represents a 2,3-dehydro-amino acid.

Finally, as explained above, a compound of formula (Ia) may be converted into a related product of formula (I) via processes of salification of the primary, secondary or tertiary basic groups present in the compounds of formula (Ia) using for this purpose pharmaceutically acceptable acids, or by salification of any carboxyl or sulphonic residues that might be present in the compounds of formula (Ia) with pharmaceutically acceptable bases.

Examples of pharmaceutically acceptable acids are monobasic and polybasic mineral acids, such as hydrochloric acid, sulphuric acid, nitric acid, phosphoric acid; or monobasic and polybasic organic acids, such as acetic acid, benzoic acid, tartaric acid, citric acid, fumaric acid, maleic acid, mandelic acid, oxalic acid, and malonic acid.

Examples of pharmaceutically acceptable salts are those with the cations of alkaline or alkaline-earth metals and preferably of sodium and magnesium, and with organic bases, such as tromethamine, D-glucosamine, lysine, arginine, tetraethyl ammonium. The R-enantiomers of the 2-arylpropionic acids of formula (Va)

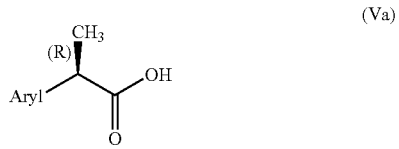

(Va)

are known compounds, characterized with respect to their S-enantiomers in that they are somewhat ineffective as inhibitors of the cyclo-oxygenase enzymes, or are prepared according to the methods described in detail in the examples which follow. Preferred R-2-arylpropionic acids of formula (V) are substituted R-2-phenyl-propionic acids where the substituting group on the phenyl ring is 2-(1-oxo-2-isoindolinyl)-, 3-phenoxy-, 3-benzoyl-, 4-thienoyl-, 4-isobutyl-, 4-hydroxy-, 4-methoxy-, 5-benzoyl-2-hydroxy-, or where the aryl group is R-2-(5-benzoyloxy-thien-2-yl)-, 2-(2-fluoro-4-biphenyl)- and R-2-(6-methoxy-naphthyl).

Particularly preferred R-2-arylpropionic acids of formula (V) are those wherein the aryl residue is the one of the R-enantiomers of ibuprofen, ketoprofen, surprofen, tiaprofen, naproxen and flurbiprofen. Said R-2-aryl-propionic acids are known compounds and are obtainable as enantiomers via processes of optical resolution of the corresponding racemic 2-arylpropionic acids (or (R,S)-2-arylpropionic acids). Methods for the total and stereospecific synthesis of individual 2-arylpropionic acids are widely described. Likewise described is the conversion of (R,S)-2-arylpropionic acids into one of the enantiomers via intermediate 2-aryl-2-propyl-ketenes.

The enantioselective syntheses of 2-aryl-propionic acids principally relates to their S-enantiomers, but may be modified to obtain the R-enantiomers via a convenient choice of the chiral auxiliary. For the use of arylalkylketones as substrates for the synthesis of α-arylalkanoic acids, see, for example, B. M. Trost and J. H. Rigby, J. Org. Chem., 14, 2936, 1978; for the a-arylation of Meldrum acids, see J. T. Piney and B. A. Rowe, Tetrah. Lett., 21, 965, 1980; for the use of tartaric acid as chiral auxiliary, see G. Castaldi et al., J. Org. Chem., 52, 3018, 1987; for the use of alpha-hydroxyesters as chiral reagents, see R. D. Larsen et al., J. Am. Chem. Soc., 111, 7650, 1989 and U.S. Pat. No. 4,940,813 and the references cited therein.

A specific process for the preparation of 2-arylpropionic acids wherein the aryl is a 5-benzoyl-2-OH-phenyl and its esters has been described in Italian patent No. 1 283 649.

An efficient method for the preparation of the R enantiomer of said acid, consists in the conversion of the chloride of (R,S)-2-(5-benzoyl-2-acetoxy)propionic acid into the 2-(5-benzoyl-2-acetoxy)prop-1-ketene, by treatment with a tertiary amine, such as dimethylethyl amine, which in turn, when is reacted with R(-)-pantolactone, yields R(-)dihydro-3-hydroxy-4,4-dimethyl-2(3H)-furanone-2-acetoxy-5-benzoylphenyl propionate as the only diastereoisomer (Myers et al., J. Am. Chem. Soc. 119, 6496, 1997 and Larsen R. D. et al., J. Am. Chem. Soc., 111, 7650 1989). The subsequent saponification with LiOH yields R-2-(5-benzoyl-2-hydroxyphenyl)-propionic acid in an effective way, avoiding the tedious procedures of optical resolution, for example by fractioned crystallization of the salts of dextro- and/or levo-dropropizine.

In a general procedure for the preparation of (R)2-arylpropionic acids of formula (Vb), mono or polysubstituted hydroxyarylketones (Vc) are reacted with a perfluorobutane-sulfonylfluoride to give the perfluorobutanesulfonate ester (Vd) wherein n is an integer from 1 to 9.

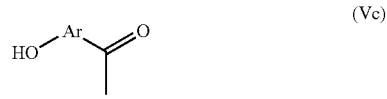

(Vc)

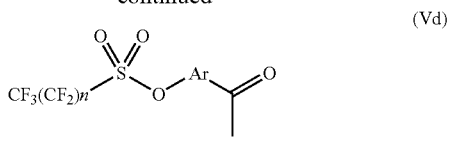
(Vd)

The compounds (Vd) undergo the Willgerodt rearrangement to give, after esterification and alfa methylation, aryl-propionic derivatives (Ve) wherein n is an integer from 1 to 9 and $R_3$ represents $C_1$-$C_4$ alkyl or $C_2$-$C_4$ alkenyl.

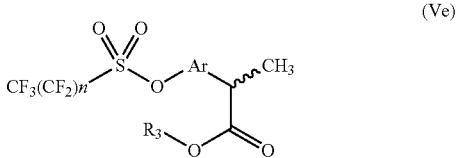
(Ve)

Compounds of formula Ve are reacted with the appropriate tributyltinR4 reagent wherein R4 is straight or branched $C_1$-$C_6$ alkyl, $C_2$-$C_6$ alkenyl or alkynyl, unsubstituted or substituted with an aryl group, to yield the corresponding (R,S) 2-arylproprionate of formula (Vf).

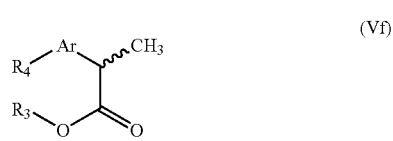
(Vf)

Alkenyl or alkynyl groups can be hydrogenated under catalytic conditions to give the corresponding saturated alkyl groups. The compounds of formula (Vf) undergo the deracemization process as described above by conversion of the corresponding acid chlorides into ketenes, which, by reaction with R(–)pantolactone and subsequent hydrolysis, yields the pure R enantiomer.

The amines of formula (VI) are known products, most are commercially available, or may be prepared using known methods.

The allyl esters of α-amino acids or ω-amino acids are known products, commercially available, or they may be prepared using known methods; see H. Waldmann and H. Kunz Liebigs Ann. Chem., 1712 (1983) or J. Org. Chem., 1989, cited previously.

For in vitro evaluation of the compounds of the invention, polymorphonucleated leucocytes were used (hereinafter referred to as PMNs) isolated from heparinized human blood, taken from consenting healthy adults, by means of sedimentation on dextrane; the mononucleated cells were removed by means of Ficoll/Hypaque, whilst the red blood cells were eliminated by treatment with hypotonic solutions. The cell vitality of the PMNs was calculated by exclusion with Tripan blue, whilst the percentage of PMNs on the cytocentrifugate was estimated after staining with Diff Quinck., in accordance with the procedure described by W. J. Ming et al., J. Immunol., 138, 1469, 1987. In each of the experiments, which will be described in details below, the pre-incubations were carried out at a temperature of 37° C., observing incubation times of 10 minutes with the compounds under examination.

In the chemotaxis experiments and in those aimed at measuring the cytosol levels of the $Ca^{++}$ ion, recombinant human interleukin-8 (rhIL-8, Pepro Tech) was used; the lyophilized protein was dissolved in HBSS (Hank's balanced salts solution) at the concentration of 100 mcg/mL, and then diluted down to a concentration of 10 ng/mL in the chemotaxis experiments, to that a concentration of 25-50 ng/mL in the evaluation of the intracellular modifications of $Ca^{2+}$ (i.e. $[Ca^{2+}]_i$) and to that a concentration of 400 ng/ml in the evaluation of tyrosine kinase activation.

During the chemotaxis assay (according to W. Falket et al., J. Immunol. Methods, 33, 239, 1980) PVP-free filters were used having a porosity of 5 mcm and microchambers made of plexiglas suitable for carrying out the replication. The microchamber, consisting of a block of plexiglas containing 48 wells having a capacity of 25 μL, was provided with a lid, in turn containing 48 pores arranged in such a way that top compartments were formed in the microchamber, which had a capacity of 50 μL once the lid was put and screwed back on the bottom part.

The compounds being studied were added at one and the same concentration in the top-level wells that contained the suspension of PMNs, and in the wells of the bottom level that contained the vehicle to which IL-8 (or, if so desired, another stimulating agent) was added or otherwise.

Table 2 below gives the results of the in vitro evaluation of certain representative compounds of formula (I) ($10^{-8}$ M), in comparison with (R)-2-(4-isobutyl-phenyl)-propionamide, as inhibitors of chemotaxis induced by IL-8.

TABLE 2

| | R' | % inhibition of chemotaxis of human PMNs stimulated by IL-8 (10 ng/mL) |
|---|---|---|
| 1 | H | 57 ± 12 |
| 2 | CH3 | 25 ± 9 |
| 3 | —CH2—CH2—OH | 20 ± 11 |
| 4 | —CH2—CH2H* | 45 ± 8 |
| 5 | L-CH(CH3)—CO2H** | 65 ± 9 |
| 6 | D-CH(CH3)—CO2H**+ | −17 ± 6 |
| 7 | L-CH(CH2OH)—CO2H*** | 12 ± 4 |
| 8 | (CH2—CH2O)2H | 40 ± 4 |
| 9 | phenyl | 9 ± 10 |
| 10 | 2-pyridyl | 36 ± 6 |
| 11 | 3-pyridyl | 11 ± 10 |
| 12 | 4-pyridyl | 61 ± 8 |

*R-ibuprophenoyl-glycine;
**R-ibuprophenoyl-L-alanine;
**+R-ibuprophenoyl-D-alanine;
***R-ibuprophenoyl-serine The results show an unexpected dependence of the activity on a number of factors, which are independent of one another. A steric contribution is evident, resulting from the stereochemistry of the amino acid acylated by the R-2-arylpropionic acid (in the case in point R-ibuprofen): after acylation with D-alanine (5) a marked "pro-kinetic" paradox effect is observed, which is quite distinct from the inhibitory effect on chemotaxis manifested by the amides with glycine (4) and with L-alanine (6).

Also the electronic effect induced on the amide carbonyl by the substituents of an aromatic and hetero-aromatic type considerably affects the activity: in contrast to the good activity of 2-pyridyl-amide and 4-pyridyl-amide (10, 12) there is a poor activity in the case of anilide (9) and of 3-pyridyl-amide (11).

The observation that, given the other substituents being the same, the presence, in the alkyl residue R' of the amides (3, 7), of a primary alcoholic group in position γ with respect to the amide carbonyl is accompanied by a decrease in the biological activity, which is restored after its etherification with the —CH$_2$—CH$_2$—OH residue (8), points towards a dependence of the potency of the biological effect upon the involvement or otherwise of the amide carbonyl in Van der Waals intramolecular bonds.

A strict dependence of the biological effects upon the absolute configuration of any R' substituents which might be present in the compounds of formula (I) is moreover demonstrated by comparing the activity of the individual diastereoisomers obtained by reaction of the enantiomers of the chloride of 2-(4-isobutyl-phenyl)propionic acid (ibuprofen) with the enantiomers of alanine. The results, reported in Table 3, show how each of the four diastereoisomers behaves in a significantly different way, presumably as a consequence of interactions of a receptor type, up to the present unknown, at the basis of the mechanism of action of these compounds.

TABLE 3

| Stereochemistry of R-ibuprophenoyl-alanine | % inhibition of leucocyte chemotaxis |
| --- | --- |
| R,L | 65 ± 9 |
| S,L | 4 ± 13 |
| S,D | 4 ± 19 |
| R,D | −17 ± 6 |

From the pharmacological evaluation of the enantiomers of the amides of ibuprofen and ketoprofen with 4-methyl-2-amino-pyridine (Table 4), it can be noted a curious discontinuity of the biological effect according to the presence or otherwise of substituents on the pyridine ring and to the consequent electronic or steric effects on the amide carbonyl.

TABLE 4

| Compound | % inhibition of chemotaxis of human PMNs stimulated by IL-8 (10 ng/mL) |
| --- | --- |
| R-2-(3-benzoylphenyl)propionamide-4-methyl-pyridine | −15 ± 25 |
| S-2-(3-benzoylphenyl)propionamide-4-methyl-pyridine | −1 ± 10 |
| R-2-(4-isobutyl-phenyl)propionamide-4-methyl-pyridine | −12 ± 2 |
| S-2-(4-isobutyl-phenyl)propionamide-4-methyl-pyridine | −3 ± 5 |

By way of example, (R,S')-2-(4-isobutyl-phenyl)-(N-carboxyethyl) propionamide inhibits, in a dose-dependent way, the chemotaxis induced by IL-8 (10 ng/mL) in the concentration range from $10^{-8}$ to $10^{-10}$ M.

The compounds of the invention are moreover capable of inhibiting the increase in the intracellular concentration of Ca$^{++}$ ions induced by IL-8, an evaluation conducted in accordance with the experimental model described by C. Bizzarri et al., Blood, 86, 2388, 1995. In addition, the compounds of the invention significantly reduce IL-8-induced tyrosine kinase activation.

As previously discussed, the compounds of the invention have not been found to inhibit the enzymes of COXs when evaluated ex vivo according to the procedure described by Patrignani et al., J. Pharmacol. Exper. Ther., 271, 1705, 1994. In addition, in almost all cases, the compounds of the invention of formula (I) do not interfere with the production of PGE$_2$ induced in murine macrophages by stimulation with lipopolysaccharides (1 mcg/mL) in the concentration range between $10^{-5}$ and $10^{-8}$ M. The inhibition of the production of PGE$_2$, which may possibly be recorded, is mostly at the limit of statistical significance, and often is lower than 15-20% of the basal value.

This insignificant inhibition of the synthesis of PGE$_2$ enables a clear differentiation of the compounds of the invention of formula (I) from the S enantiomers of 2-arylpropionic acids and from their amides, which, on the contrary, due to the marked inhibition of the synthesis of PGE$_2$, constitute, for the murine macrophages themselves, a stimulus towards an amplification of the synthesis of TNF-α.

Notably, an amplification in TNF-α synthesis contributes to amplifying activation of the neutrophils and to favouring their chemotaxis, as well as constituting a stimulus to the synthesis of IL-8. For certain of the compounds of the invention of formula (I) there is moreover recorded an inhibitory effect in regard to the synthesis of TNF-α, which is normally stimulated in macrophages by LPSs, an inhibitory effect that is found also in regard to the synthesis of cytokine itself after stimulation with H$_2$O$_2$.

In view of the above experimental evidence and of the involvement of IL-8 and its affines as the most important mediators and promotors of the infiltration of neutrophils in diseases, such as psoriasis (R. J. Nicholoff et al., Am. J. Pathol., 138, 129, 1991), rheumatoid arthritis (M. Selz et al., J. Clin. Invest., 87, 463, 1981), ulcerative cholitis (Y. R. Mahla et al., Clin. Sci., 82, 273, 1992), acute respiratory insufficiency and idiopathic fibrosis (E. J. Miller, cited previously, and P. C. Carré et al., J. Clin. Invest., 88, 1882, 1991), glomerular nephritis (T. Wada et al., J. Exp. Med., 180, 1135, 1994), the compounds of the invention of formula (I) are used for the treatment of these diseases and for the prevention and the treatment of damages caused by ischaemia and reperfusion (N. Sekido. et al., Nature, 365, 654, 1993).

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the amides of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the invention can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the amide compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Liquid forms, including the injectable compositions described herebelow, are always stored in the absence of light, so as to avoid any catalytic effect of light, such as hydroperoxide or peroxide formation. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the amide derivative of formula I in such compositions is typically a minor component, frequently ranging between 0.05 to 10% by weight with the remainder being the injectable carrier and the like. The mean daily dosage will depend upon various factors, such as the seriousness of the disease and the conditions of the patient (age, sex and weight). The dose will generally vary from 1 mg or a few mg up to 1500 mg of the compounds of formula (I) per day, optionally divided into multiple administrations. Higher dosages may be administered also thanks to the low toxicity of the compounds of the invention over long periods of time.

The above described components for orally administered or injectable compositions are merely representative. Further materials as well as processing techniques and the like are set out in Part 8 of "Remington's Pharmaceutical Sciences Handbook", 18$^{th}$ Edition, 1990, Mack Publishing Company, Easton, Pa., which is incorporated herein by reference.

The compounds of this invention can also be administered in sustained release forms or from sustained release drug delivery systems. A description of representative sustained release materials can also be found in the incorporated materials in the Remington's Handbook as above.

The present invention shall be illustrated by means of the following examples which are not construed to be viewed as limiting the scope of the invention.

In the description of the compounds of the invention of formula (I), the convention has been adopted of indicating the absolute configurations of any chiral substituents that may be present in the substituent R' of said compounds with prime signs (e.g., R' S', S" etc.).

Examples of abbreviations are THF for tetrahydrofuran, DMF for dimethylformamide, HOBT for 1-hydroxy-benzothiazole, DCC for dicyclohexylcarbodiimide.

EXAMPLES

Example 1

(R,S')-2-[(4'-isobutyl)phenyl]-N-(2-carboxyethyl) propionamide

To a solution of R(−)-ibuprofen (5 g; 24.24 mmol) in DMF (20 mL), cooled approximately to a temperature T=0° C., 3 g of HOBT (22.2 mmol) were added under stirring. After 15 minutes, a mixture of L-alanine methyl ester hydrochloride (3.2 g; 22.2 mmol) and triethyl amine (3 mL) in DMF (5 mL) was added; finally, DCC was added in successive portions for a total of 5 g (24.24 mmol). The mixture was kept under stirring for two hours at a temperature T=0° C. and then, overnight, at room temperature. After elimination by filtration of the dicyclohexylurea precipitate, the filtrate was diluted with ethyl acetate (50 mL). The organic phase was washed with a solution of 10% citric acid (2×20 mL), with a saturated solution of $NaHCO_3$ (2×20 mL), and finally with a saturated solution of NaCl (20 mL). After drying on $Na_2SO_4$ by evaporation of the solvents at low pressure, a residue was obtained (3.86 g), which, suspended in hexane (60 mL) and kept under stirring overnight, enabled separation of a white crystalline precipitate of (R,S')-2-[(4'-isobutyl)phenyl]-N-(2-methoxycarbonylethyl)propionamide (4.9 g, 16.84 mmol).

To a solution of 2 g (6.87 mmol) of the latter compound in dioxane (9 mL) an equal volume of NaOH 1N (9 mL) was added and the mixture was kept under stirring at room temperature overnight. After dilution with water and ice (130 mL), it was acidified with concentrated $H_2SO_4$ to a clearly acidic pH. After exhaustive extraction of the aqueous phase with $CH_2Cl_2$ (4×20 mL), the organic extracts were combined, washed with a saturated solution of NaCl (20 mL), dried on $Na_2SO_4$ and evaporated at low pressure to yield a residue which, once crystallized using ethyl ether (30 mL), yielded (R,S')-2-[(4'-isobutyl)phenyl]-N-(2-carboxyethyl)propionamide (1.81 g, 6.52 mmol), m.p. 125-128° C., $[\alpha]_D$=−46 (c=1%; $CH_3OH$);

$^1$H-NMR ($CDCl_3$): δ 7.25-7.1 (m, 4H); 5.85 (bs, CONH); 4.52 (m, 1H); 3.62 (q, 1H, J=14 Hz, $J_2$=7 Hz); 2.47 (d, 2H, J=7 Hz); 1.85 (m, 1H); 1.53 (d, 3H, J=7 Hz); 1.35 (d, 3H, J=7 Hz); 0.93 (d, 6H, J=7 Hz).

Alternatively, if so desired, the hydrolysis of the methyl ester may be conducted also using trimethylsilyl iodide, for example in chloroform.

A solution of 1.71 mmol of the ester in $CHCl_3$, to which 2.56 mmol of trimethylsilyl iodide were added, was heated for a few hours to 50° C.; then the process of the reaction was interrupted by cooling to room temperature (so as to minimize the possible formation of by-products). After evaporation of the solvents, the crude product of reaction was taken up again with ethyl ether; the organic phase was extracted with NaOH 1N (2×15 mL); the basic aqueous extracts were combined, acidified and de-stained by treatment with sodium thiosulphate. The aqueous phase was then extracted with $CH_2Cl_2$ (2×15 mL), and the organic extracts, which were combined after the usual treatment (washing with a saturated solution of NaCl, drying on $Na_2SO_4$), yielded the desired (R,S')-2-[(4'-isobutyl)phenyl]-N-(2-carboxyethyl)propionamide.

Example 2

By substituting, in the procedure of Example 1, L-alanine with D-alanine methyl ester and with glycine methyl ester the following were prepared: (R,R')-2-[(4'-isobutyl)phenyl]-N-(2"-carboxyethyl)propionamide, as a pale yellow oil $[\alpha]_D$=+5 (c=0.5%; $CH_3OH$)

$^1$H-NMR ($CDCl_3$): δ 7.20-7.07 (m, 4H); 5.97 (bs, CONH); 4.45 (m, 1H); 3.60 (m, 1H); 2.45 (d, 2H, J=7 Hz); 1.85 (m, 1H); 1.53 (m, 3H); 1.35 (m, 3H); 0.91 (d, 6H, J=7 Hz);

R(−)-2-[(4'-isobutyl)phenyl]-N-carboxymethyl propionamide, m.p. 87-90° C.

$^1$H-NMR ($CDCl_3$): δ 7.23-7.07 (m, 4H); 5.93 (bs, CONH); 4.13-3.93 (m, 2H); 3.63 (q, 1H, $J_1$=8 Hz, J2=15 Hz); 2.45 (d, 2H, J=7 Hz); 1.87 (m, 1H); 1.53 (d, 3H, J=7 Hz); 0.93 (d, 6H, J=7 Hz).

Example 3

(R)—N-[2'-(4"-isobutylphenyl)propanoyl]-2-amino acrylic acid

Using L-cysteine ethyl ester in the procedure of Example 1, (R,R')-2-[(4'-isobutyl)phenyl]-N-2"-(3"-mercapto-carboxyethyl)propionamide was obtained. In an inert-gas atmosphere, to a solution of 0.3 g (0.89 mmol) of this compound in anhydrous $CH_2Cl_2$ (24 mL) cooled to a temperature T=−10° C., a 1M solution of $BBr_3$ in $CH_2Cl_2$ (6 mL) was added dropwise under stirring. The reaction mixture was kept under stirring at a temperature T=−10° C. for one hour and then at room temperature for six hours. The mixture was then diluted with water (20 mL), the two phases were separated, and the aqueous phase was re-extracted with $CH_2Cl_2$. The combined organic extracts were washed with a saturated solution of $NaHCO_3$ (3×20 mL). The basic aqueous phase was then acidified with HCl 2N to pH=2 and extracted with $CH_2Cl_2$ (3×10 mL). The combined organic extracts were dried on $Na_2SO_4$ and evaporated to yield (R)N-[2'-(4"-isobutylphenyl)propanoyl]-2-amino acrylic acid (0.080 g, 0.29 mmol) as an opalescent oil;

$^1$H-NMR ($CDCl_3$): δ 7.4-7.2 (m, 4H); 6.81 (s, 1H); 6.1 (s, 1H); 3.80 (m, 1H); 3.11 (s, 3H); 3.03 (s, 3H); 2.60 (m, 2H); 2.01 (m, 1H); 1.70 (d, 3H, J=7 Hz); 1.07 (d, 6H, J=7 Hz).

Example 4

Methyl R—N-[2'-(4"-isobutylphenyl)propanoyl]-2-amino acrylate

The product was obtained by β-elimination in the presence of potassium tert-butoxide (1.1 equiv.) in anhydrous ethyl ether starting from (R,R')-2-[(4'-isobutyl)phenyl]-N-2"-(3"-mercapto-carboxymethyl)propionamide (at T=0° C.). After dilution with 1.11 equiv. of AcOH in ethyl ether, repartition with a saturated solution of $NaH_2PO_4$ in water, separation and drying of the organic phase, methyl (R)—N-[2'-(4"-isobutylphenyl)propanoyl]-2-amino acrylate was obtained, after evaporation, in the form of a pale yellow oil;

$^1$H-NMR ($CDCl_3$): δ 7.25-7.15 (m, 4H); 6.57 (s, 1H); 5.83 (s, 1H); 3.77 (s, 3H); 3.63 (m, 1H); 2.47 (d, 2H, J=7 Hz); 1.87 (m, 1H); 1.53 (d, 3H, J=7 Hz); 0.93 (d, 6H, J=7 Hz).

By performing the same reaction in the presence of an equivalent amount of water at 0° C., the free acid of the previous example was obtained.

Example 5

R(−)-2-[(4'-isobutyl)phenyl]-N-(2"-hydroxyethoxyethyl)propionamide

A solution of R(−)-ibuprofen (2 g; 9.69 mmol) in thionyl chloride (4 mL) was heated for 3 hours at the reflux temperature; after cooling to room temperature, the solvent was evaporated at low pressure, taking up the residue twice in succession with dioxane and evaporating the solvents in high-vacuum conditions to eliminate the residual traces of thionyl chloride. The oily yellow residue (2.16 g; 9.6 mmol) of R(−)-ibuprophenoyl chloride thus obtained was dissolved in anhydrous $CH_2Cl_2$ (15 mL). The solution was added dropwise, at room temperature to a solution of 2-(2-aminoethoxy)ethanol (0.97 mL; 9.7 mmol) and triethyl amine (1.35 mL; 9.7 mmol) in anhydrous $CH_2Cl_2$ (15 mL). Stirring of the reaction mixture was continued overnight at room temperature; then the mixture was diluted with $CH_2Cl_2$ (30 mL), the organic phase was washed with HCl 1N (2×10 mL) and with a saturated solution of NaCl. After drying on $Na_2SO_4$ and evaporation of the solvent at low pressure, a residue was obtained, which was purified via flash chromatography (eluent $CH_2Cl_2/CH_3OH$ 98:2) to yield, as a transparent oil, 1.87 g of R(−)-2-[(4'-isobutyl)phenyl]-N-(2"-hydroxyethoxyethyl)-propionamide; $[\alpha]_D$=−3.2 (c=3%; EtOH).

$^1$H-NMR ($CDCl_3$): δ 7.23 (d, 2H, J=7 Hz); 7.13 (d, 2H, J=7 Hz); 5.77 (bs, CONH); 3.75-3.33 (m, 9H); 2.47 (d, 2H, J=7 Hz); 1.85 (m, 1H); 1.63 (bs, OH); 1.53 (d, 3H, J=7 Hz); 0.93 (d, 6H, J=7 Hz).

Example 6

Using, in the procedure of the previous example, (S)-1-methyl-2-(2'-hydroxyethoxy)-ethyl amine, (R,S')-2-[(4"-isobutyl)phenyl]-N-[1'-methyl-2'-(2""-hydroxy-ethoxy)ethyl]propionamide was obtained; $[\alpha]_D$=−16 (c=1%; $CH_3OH$);

$^1$H-NMR ($CDCl_3$): δ 7.22 (d, 2H, J=7 Hz); 7.13 (d, 2H, J=7 Hz); 5.55 (bs, CONH); 4.17 (m, 1H); 3.65 (m, 2H); 3.55 (m, 4H); 3.40 (m, 1H); 2.47 (d, 2H, J=7 Hz); 2.05 (bs, OH); 1.85 (m, 1H); 1.53 (d, 3H, J=7 Hz); 1.1 (d, 3H, J=7 Hz); 0.93 (d, 6H, J=7 Hz).

Using, in the procedure of the previous example, (R)-1-methyl-2-(2'-hydroxyethoxy)ethyl amine, (R,R')-2-[(4"-isobutyl)phenyl]-N-[1'-methyl-2'-(2'"-hydroxyethoxy)ethyl]propionamide was obtained.

Example 7

Using, in the procedure of Example 1, a heterocyclic amine selected in the group consisting in 2-amino-pyridine, 3-amino-pyridine and 4-amino-pyridine, the following were obtained, respectively: R(−)-2-(4'-isobutyl)phenyl-N-(2'-pyridyl)propionamide, in the form of a transparent oil; $[\alpha]_D$=−56 (c=1%; $CH_3CH_2OH$);

$^1$H-NMR ($CDCl_3$): δ 8.25 (m, 2H); 7.71 (m, 2H); 7.22 (d, 2H, J=7 Hz); 7.13 (d, 2H, J=7 Hz); 7.05 (bs, CONH); 3.70 (m, 1H); 2.45 (d, 2H, J=7 Hz); 1.85 (m, 1H); 1.53 (d, 3H, J=7 Hz); 0.93 (d, 6H, J=7 Hz); R(−)-2-[(4'-isobutyl)phenyl]-N-(3"-pyridyl)propionamide, in the form of a waxy solid; $[\alpha]_D$=−96 (c=1%; $CH_3CH_2OH$);

$^1$H-NMR (DMSO-$d_6$): δ 8.7 (s, 1H); 8.22 (d, 1H, J=5 Hz); 8.03 (m, 1H); 7.13 (m, 3H); 7.13 (d, 2H, J=7 Hz); 3.80 (m, 1H); 2.45 (d, 2H, J=7 Hz); 1.80 (m, 1H); 1.43 (d, 3H, J=7 Hz); 0.85 (d, 6H, J=7 Hz);

R(−)-2-[(4'-isobutyl)phenyl]]-N-(4'-pyridyl)propionamide.

Each of these amides can then be converted, if so desired, into the corresponding salts according to procedures that are well known to the art, to obtain, for example: R(−)-2-[(4'-isobutyl)phenyl]-N-(4"-pyridyl)propionamide hydrochloride, m.p. 95-100° C. $[\alpha]_D=-54$ (c=0.2%; $CH_3OH$);
$^1$H-NMR (DMSO-d6): δ 10.91 (s, 1H), 8.87 (d, 2H, J=7 Hz); 7.83 (d, 2H, J=7 Hz); 7.37 (d, 2H, J=7 Hz); 7.20 (d, 2H, J=7 Hz); 3.97 (m, 1H); 2.45 (d, 2H, J=7 Hz); 1.90 (m, 1H); 1.50 (d, 3H, J=7 Hz); 0.95 (d, 6H, J=7 Hz).

In like manner, by acylation of R-ketoprofen, the following was obtained:

R(−)-2-[(5'-benzoyl)phenyl]-N-(2'-pyridyl)propionamide hydrochloride as a white powder; $[\alpha]_D=-6$ (c=1%; $CH_3CH_2OH$);
$^1$H-NMR ($CDCl_3$): δ 12.65 (bs, NH+); 8.75 (m, 1H); 8.2 (m, 1H); 7.93-7.33 (m, 1H); 4.20 (m, 1H); 1.67 (d, 3H, J=7 Hz).

Example 8

R(−)-2-(4'-isobutyl)phenyl-N-methyl propionamide

By reacting a solution of R-ibuprophenoyl chloride in dioxane with an aqueous solution of N-methylamine in Schotten-Baumann conditions, R(−)-2-(4'-isobutyl)phenyl-N-methyl propionamide was obtained in the form of a pale yellow oil; $[\alpha]_D=-21$ (c=1%; $CH_3CH_2OH$).
$^1$H-NMR ($CDCl_3$): δ 7.22 (d, 2H, J=7 Hz); 7.13 (d, 2H, J=7 Hz); 5.30 (bs, CONH); 3.53 (m, 1H); 2.73 (d, 3H, J=7 Hz); 2.45 (d, 2H, J=7 Hz); 1.87 (m, 1H); 1.53 (d, 3H, J=7 Hz); 0.93 (d, 6H, J=7 Hz).

Example 9

Using (R)-ketoprofen in the procedure of Example 1, the following was obtained: (R)(−)-2-[(5'-benzoyl)phenyl]-N-carboxymethyl propionamide, in the form of a foamy white solid; $[\alpha]_D=-9$ (c=1%; $CH_3OH$);
$^1$H-NMR ($CDCl_3$): δ 7.81-7.30 (m, 9H); 6.17 (bs, CONH); 4.1-3.25 (m, 4H); 1.47 (d, 3H, J=7 Hz).

Example 10

Using the methyl esters of cis- and trans-4-aminocyclohexancarboxylic acids in the procedure of Example 1, the following were prepared; cis-(R)-2-[(4'-isobutyl)phenyl]-N-(4'carboxy-cyclohexyl)propionamide; and trans-(—R)-2-[(4'-isobutyl)phenyl]-N-(4' carboxy-cyclohexyl) propionamide.

Example 11

To a solution of 0.32 g of (R)-2-(2-acetoxy-5-benzoyl) phenyl-propionic acid in 10 mL of AcOEt (dried on molecular sieves) 0.185 g of carbonyldiimidazole were added under stirring; then, after approximately one hour, 0.2 g of L-alaninoyl-glycine allyl ester were added. The mixture was kept for 12 hours at room temperature; the reaction mixture was diluted with AcOEt (5 mL) and was washed repeatedly with $H_2SO_4$2N, water, 5% $NaHCO_3$, and again water to neutrality, and then evaporated to dryness to yield, after purification on a silica-gel column, 0.41 g of (R)-2-(2-acetoxy-5-benzoyl) phenyl-propionil-L-alaminoyl-glycine allyl ester.

To a solution of 0.24 g of the ester (0.05 mM) in THF (10 mL), kept under stirring in an inert-gas atmosphere, 60 mg of tetra(triphenylphosphine)palladium (0) and 0.5 mL of morpholine were added in succession. After approximately one hour, the solvent was evaporated in vacuum conditions. The residue was dissolved in ethyl acetate; the solution was washed repeatedly with $H_2SO_4$2N and water to neutrality, to yield, after drying on sodium sulphate, evaporation to dryness, and percolation of the residue on a column of silicic acid, 0.12 g of (R)-2-(2-acetoxy-5-benzoyl)phenyl-propanoyl-L-alaminoyl-glycine.

By "silicic acid" is meant a batch of $SiO_2$ for column chromatography, which, after repeated suspensions in HCl 6 N, has been washed to neutrality and up to disappearance of traces of Cl-ions in the eluate ($AgNO_3$ assay), and then reactivated by heating to 120° C. for at least 24 hours.

Using, according to the same procedure, (R)-2-(2-fluoro-4-biphenyl)-propionic acid, (R)-2-[(4'-methoxy)phenyl]-propionic acid, (R)-2-(2-hydroxy-5-benzoyl)-phenyl-propionic acid, (R)-2-(3-phenoxyphenyl)-propionic acid, the allyl esters of phenylglycine, glycine and L-alanine, L-phenylalanine, L-alaminoyl-glycine, glycinoyl-L-alanine, the following were obtained:

R-2-(2-fluoro-4-biphenyl)-propanoyl-glycine;

(R)-2-(2-hydroxy-5-benzoyl)phenyl-propanoyl-glycine;

(R)-2-[(4'-methoxy)phenyl]-propanoyl-L-alanine;

(R)-2-(2-hydroxy-5-benzoyl)phenyl-propanoyl-glycinoyl-L-alanine;

(R)-2-(2-hydroxy-5-benzoyl)phenyl-propanoyl-L-alaminoyl-glycine;

(R)-2-(2-hydroxy-5-benzoyl)phenyl-propanoyl-L-phenylalanine;

(R)-2-(3-phenoxyphenyl)-propanoyl-phenylglycine;

(R)-2-(3-phenoxyphenyl)-propanoyl-glycine.

Example 12

By reaction of an R-2-arylpropionic acid selected in the group consisting in ibuprofen, suprofen, tiaprofen, flurbiprofen, and naproxen with 4-aminopyridine with carbonylimidazole in accordance with the procedure of Example 11, the corresponding imidazolides were obtained, which were reacted in situ with 4-amino-pyridine and 1-aminoethyl-4-(4', 4"-difluorophenyl)-methyl-piperazine to obtain:

N-[-2[4-(4',4"-difluorophenyl)-methyl-piperazin-1-yl) ethyl]-R-2-(4-isobutylphenyl)-propionamide;

N-(pyrid-4-yl)-R-2μ-fluoro-4-biphenyl)propionamide;

N-(pyrid-4-yl)-R-2(6-methoxynaphthyl)propionamide;

N-(pyrid-4-yl)-R-2(4-thienoylphenyl)propionamide;

N-(pyrid-4-yl)-R-2(5-benzoyl-thien-2-yl)propionamide.

Example 13

By reaction of the imidazolide of R-ibuprofen with an allyl ester of N-methylglycine, 3-amino-1,5 pentanedioic acid, N-(carboxymethyl)glycine and N-carboxyethyl-glycine according to the procedure of Example 11, the following were obtained, respectively:

N—[R-2-(4-isobutylphenyl)propanoyl]-N-methylglycine;

N—[R-2-(4-isobutylphenyl)propanoyl]-iminodiacetic acid;

R-3-aza-3-[2-(4-isobutylphenyl)propanoyl)]-1,6-hexanedioic acid;

N-3-[2-(4-isobutylphenyl)propanoyl)]-1,5-pentanedioic acid; and allyl esters thereof.

By reaction of the methyl esters of sarcosine, N-allylglycine and N-propargylglycine with R-ibuprofen in accordance with the procedure of Example 1, the following were obtained:

N—[R-2-(4-isobutylphenyl)propanoyl]-N-methyl glycine;

N—[R-2-(4-isobutylphenyl)propanoyl]-N-allyl glycine;

N—[R-2-(4-isobutylphenyl)propanoyl]-N-propargyl glycine; and methyl esters thereof.

Example 14

Using, in Example 11, L-S-carboxymethylcysteine diallyl ester and the allyl esters of L-leucine, L-methionine, L-O-methylserine and serine by reaction with the imidazolides of R-ibuprofen, R-ketoprofen and R-Indoprofen, the allyl esters of the corresponding amides were obtained, which by treatment with Pd(0)/morpholine, were converted into the following free acids:

N—[R-2(4-isobutylphenyl)-propanoyl]-L-S-carboxymethyl cysteine;

N—[R-2-(3-benzoylphenyl)propanoyl]-L-S-carboxymethyl cysteine;

N—[R-2-(4-isobutylphenyl)-propanoyl]-L-leucine;

N—[R-2-(3-benzoylphenyl)propanoyl]-L-leucine;

N—[R-2-[1-oxo-2-isoindolinyl-phenyl)propanoyl]-L-leucine;

N—[R-2(4-isobutylphenyl)-propanoyl-]-L-O-methyl serine;

N—[R-2-(3-benzoylphenyl)propanoyl-]-L-O-methyl serine;

N—[R-2-[1-oxo-2-isoindolinyl-phenyl)propanoyl]-L-O-methyl serine;

N—[R-2-(4-isobutyl)phenyl)propanoyl]-L-serine;
$^1$H-NMR (CDCl$_3$): δ 7.3-7.0 (m, 4H); 6.45 (bs, 1H); 4.5 (m, 1H); 4.1-4.0 (m, 1H); 3.9-3.5 (m, 2H); 2.5-2.3 (m, 3H); 1.85 (m, 1H); 1.5 (m, 3H); 0.9 (d, 6H).

Example 15

Preparation of Intermediate Amines

S-1-methyl-2-(2'-hydroxyethoxy)ethyl amine

A solution of tert-butyl dicarbonate (1.4 g; 6.49 mmol) in anhydrous THF (15 mL) was added dropwise to a solution of S(+)-2-amino-1-propanol (0.5 mL; 6.42 mmol) in anhydrous THF (15 mL), stirred, and cooled to about 0° C. The mixture was then kept under stirring overnight at room temperature. The solvent was evaporated; the residue was taken up with CH$_2$Cl$_2$ (55 mL); the organic phase was washed with a 5% solution of NaH$_2$PO$_4$ (3×10 mL), and was dried on Na$_2$SO$_4$. After evaporation of the solvent at low pressure, 0.965 g (5.5 mmol) of S(−)-N-tert-butoxycarbonyl-2-amino-1-propanol were obtained; [α]$_D$=−7.5 (c=1.1%; CH$_3$OH).

To a solution of 0.225 g (1.3 mmol) of this compound in anhydrous DMF (7 mL), cooled to a temperature T=0° C., the following were added in order: NaH (94 mg; 2.34 mmol, 60% suspension), and, after 20 minutes, 2-(2-bromoethoxy)tetrahydro-2H-pyrane (0.24 mL, 1.59 mmol) and tetra-N-butylammonium iodide (48 mg, 0.13 mmol). The reaction mixture was left to heat up spontaneously to room temperature, and stirring was continued overnight. It was then cooled down to 0° C. before dropwise addition of CH$_3$OH to decompose the excess reagents. It was then diluted with water; the aqueous phase was extracted with CH$_2$Cl$_2$ (2×10 mL); the organic extracts were combined and washed with a saturated solution of NaCl (2×10 mL), dried on Na$_2$SO$_4$, and evaporated at low pressure. The crude residue was purified by means of column chromatography (eluent: CHCl$_3$/CH$_3$OH/pyridine 98:2:1) to obtain 0.184 g of S-(−)-N-tert-butoxycarbonyl-3-(2'-tetrahydropyranyloxyethoxy)-2-propyl amine in the form of a transparent oil; [α]$_D$=−11.7 (c=1%; CH$_3$CH$_2$OH).

By addition of trifluoroacetic acid (0.06 mL) to a solution of the compound in anhydrous CH$_2$Cl$_2$ (10 mL), kept overnight at room temperature, after dilution with water (5 mL), separation of the phases, alkalinization of the aqueous phase at pH=10 with NaOH 1N, re-extraction with dichloromethane, and evaporation of the solvent, a residue of S-1-methyl-2-(2'-hydroxyethoxy)-ethyl amine was obtained. Using the same procedure, starting from R(−)-2-amino-1-propanol, R-1-methyl-2-(2'-hydroxyethoxy)ethyl amine was prepared.

Example 16

Preparation of Compounds Listed in Tables

A) Preparation of Compounds Listed in Table 4

Using, according to the procedure of Example 1, the individual enantiomers S-ibuprofen, R-ibuprofen, S-ketoprofen and R-ketoprofen by reaction with 4-methyl-2-amino-pyridine, the following were obtained: R(−)-2-[(4'-isobutyl)phenyl]-N-(4"-methyl-2"-pyridyl)propionamide in the form of a transparent oil; [α]$_D$=−93 (c=1%; CH$_3$CH$_2$OH);
$^1$H-NMR (CDCl$_3$): δ 8.13 (s, 1H); 8.07 (m, 1H); 7.95 (bs, CONH); 7.25 (d, 2H, J=7 Hz); 7.13 (d, 2H, J=7 Hz); 6.83 (d, 1H, J=7 Hz); 3.71 (m, 1H); 2.45 (d, 3H, J=7 Hz); 2.35 (s, 3H); 1.87 (m, 1H); 1.60 (d, 3H, J=7 Hz); 0.93 (d, 6H, J=7 Hz); S(+)-2-[(4'-isobutyl)phenyl]-N-(4"-methyl-2"-pyridyl)propionamide in the form of a transparent oil; [α]$_D$=+98 (c=1.2%; CH$_3$CH$_2$OH);
$^1$H-NMR (CDCl$_3$): δ 8.13 (s, 1H); 8.07 (m, 1H); 7.93 (bs, CONH); 7.25 (d, 2H, J=7 Hz); 7.13 (d, 2H, J=7 Hz); 6.83 (d, 1H, J=7 Hz); 3.75 (m, 1H); 2.45 (d, 3H, J=7 Hz); 2.35 (s, 3H); 1.87 (m, 1H); 1.60 (d, 3H, J=7 Hz); 0.93 (d, 6H, J=7 Hz);
R(−)-2-[(5'-benzoyl)phenyl]-N-(4"methyl-2"-pyridyl) propionamide in the form of a foamy white solid; [α]$_D$=−83.4 (c=1%; CH$_3$CH$_2$OH);
$^1$H-NMR (CDCl$_3$): δ 8.55 (bs, CONH); 8.15 (s, 1H); 8.05 (m, 1H); 7.87-7.43 (m, 9H); 6.93 (d, 1H, J=7 Hz); 3.85 (m, 1H); 2.40 (s, 3H); 1.65 (d, 3H, J=7 Hz); S(+)-2-[(5'-benzoyl) phenyl]-N-(4"-methyl-2"-pyridyl)propionamide in the form of a clear yellow solid; [α]$_D$=+87 (c=1; CH$_3$CH$_2$OH);
$^1$H-NMR (CDCl$_3$): δ 8.88 (bs, CONH); 8.2 (s, 1H); 8.05 (m, 1H); 7.85-7.43 (m, 9H); 6.93 (d, 1H, J=7 Hz); 3.90 (m, 1H); 2.40 (s, 3H); 1.60 (d, 3H, J=7 Hz).

B) Preparation of Compounds Listed in Table 3

(S, R')-2-[(4'-isobutyl)phenyl]-N-(2-carboxyethyl)propionamide; m.p. 118-121° C.; [α]$_D$=+39 (c=0.2%; CH$_3$OH);
$^1$H-NMR (CDCl$_3$): δ 7.22 (d, 2H, J=7 Hz); 7.13 (d, 2H, J=7 Hz); 5.85 (bs, CONH); 4.55 (m, 1H); 3.60 (m, 1H); 2.47 (d, 2H, J=7 Hz); 1.87 (m, 1H); 1.53 (d, 3H, J=7 Hz); 1.35 (d, 3H, J=7 Hz); 0.93 (d, 6H, J=7 Hz);

(S,S')-2-[(4'-isobutyl)phenyl]-N-(2-carboxyethyl)propionamide, m.p. 85-87° C.; $[\alpha]_D$=−2.8 (c=0.5%; $CH_3OH$);

$^1$H-NMR ($CDCl_3$): δ 7.22-7.10 (m, 4H); 6.85 (bs, CONH); 4.53 (m, 1H); 3.6 (m, 1H); 2.47 (d, 2H, J=7 Hz); 1.87 (m, 1H); 1.55 (d, 3H, J=7 Hz); 1.40 (d, 3H, J=7 Hz); 0.93 (d, 6H, J=7 Hz).

By reaction of the individual isomers of ibuprofenoyl chloride with aniline, the following were obtained:

S(+)-2-[(4'-isobutyl)phenyl]-N-phenyl propionamide: m.p. 117-120° C.; $[\alpha]_D$=+93 (c=1; $CH_3CH_2OH$);

$^1$H-NMR ($CDCl_3$): δ 7.45-6.97 (m, 10H); 3.70 (q, 1H, J1=15 Hz, J2=7 Hz); 2.45 (d, 3H, J=7 Hz); 1.87 (m, 1H); 1.60 (d, 3H, J=7 Hz); 0.93 (d, 6H, J=7 Hz);

R(−)-2-(4'-isobutyl)phenyl-N-phenyl propionamide: m.p. 118-120° C.; $[\alpha]_D$=−86 (c=1%; $CH_3CH_2OH$);

$^1$H-NMR ($CDCl_3$): δ 7.43 (m, 2H); 7.30 (m, 3H); 7.17 (m, 2H); 7.05 (m, 3H); 3.70 (m, 1H); 2.45 (d, 2H, J=7 Hz); 1.87 (m, 1H); 1.53 (d, 3H, J=7 Hz); 0.93 (d, 6H, J=7 Hz).

C) R(−)-2-(4'-isobutyl)phenyl-N-(2'-hydroxyethyl) propionamide (Table 2)

To a solution of R-ibuprofen (0.25 g, 1.21 mmol)) in anhydrous ethyl acetate, 0.11 equivalents of N,N'-carbonyl-diimidazole were added, at room temperature and under stirring. After 3 hours at room temperature, without isolating the intermediate R-ibuprofenoyl imidazolide, a solution of 0.11 equivalent of 2-amino-ethanol in anhydrous AcOEt was added. Stirring was continued for 6 hours at room temperature, and then the organic phase was distributed by repartition with an aqueous solution of $H_2SO_4$2N. The organic phases were washed to neutrality with a saturated solution of NaCl and dehydrated on $Na_2SO_4$. After evaporation of the solvent, R(−)-2-(4'-isobutyl)phenyl-N-(2'-hydroxyethyl)propionamide was obtained in the form of a pale yellow oil;

$^1$H-NMR ($CDCl_3$): δ 7.22 (d, 2H, J=7 Hz); 7.13 (d, 2H, J=7 Hz); 5.80 (bs, CONH); 3.67 (m, 2H); 3.55 (m, 1H); 3.35 (m, 2H); 2.85 (bs, OH); 2.45 (d, 2H, J=7 Hz); 1.87 (m, 1H); 1.55 (d, 3H, J=7 Hz); 0.93 (d, 6H, J=7 Hz).

E) Using the Procedure of the Above Preparation D) and L- and D-alaninol as the Amines, the Following were Obtained (R,R')-2-[(4'-isobutyl)phenyl]-N-(3"-hydroxyprop-2"-yl) propionamide: m.p. 71-74° C.; $[\alpha]_D$=+9.2 (c=0.5%; $CH_3OH$);

$^1$H-NMR ($CDCl_3$): δ 7.22 (d, 2H, J=7 Hz); 7.13 (d, 2H, J=7 Hz); 5.43 (bs, CONH);

4.00 (m, 1H); 3.6-3.35 (m, 3H); 2.45 (d, 2H, J=7 Hz); 1.85 (m, 1H); 1.47 (m, 4H); 1.05 (d, 3H, J=7 Hz); 0.93 (d, 6H, J=7 Hz);

(R,S')-2-[(4'-isobutyl)phenyl]-N-(3"-hydroxyprop-2-yl) propionamide: m.p. 75° C.; $[\alpha]_D$=−12 (c=0.5%; $CH_3OH$);

$^1$H-NMR ($CDCl_3$): δ 7.22 (d, 2H, J=7 Hz); 7.13 (d, 2H, J=7 Hz); 5.43 (bs, CONH); 4.01 (m, 1H); 3.35 (m, 4H); 2.45 (d, 2H, J=7 Hz); 1.87 (m, 1H); 1.53 (d, 3H, J=7 Hz); 1.05 (d, 3H, J=7 Hz); 0.93 (d, 6H, J=7 Hz).

Example 17

General Procedure for the Synthesis of 2-arylpropionic Acids and Related R Enantiomers 17a—Deracemization Process of 2-arylpropionic Acids of Formula Va (R)-2-(2-hydroxy-5-benzoyl)phenyl-propionic acid and (R)-2-(2-acetoxy-5-benzoyl)phenyl-propionic acid A suspension of finely ground K2CO$_3$ (2.48 g; 18 mmol) in a solution of (R,S)-2-(2-hydroxy-5-benzoyl-phenyl)-propionic acid (2 g; 7.4 mmol) in anhydrous acetone (35 mL) was kept under vigorous stirring at room temperature for 30 minutes; then acetic anhydride (2.78 mL; 29.5 mmol) was added dropwise. Upon termination of dripping, stirring was continued for 12 hours at room temperature. The product was filtered from the bottom body, and the resulting solution was evaporated to dryness at low pressure.

The solution of the residue in $CH_2Cl_2$ was washed repeatedly with water to disappearance of residues of acetic anhydride. The organic phase was dried on $Na_2SO_4$ and evaporated to dryness. A solution of the residue in THF:$H_2O$ 1:1 (30 mL) was left under stirring overnight. The subsequent evaporation of the solvents at low pressure yielded 2-(2-acetoxy-5-benzoylphenyl)-propionic acid in the form of a pale yellow oil (1.85 g; 5.92 mmol);

$^1$H-NMR ($CDCl_3$): δ 8.0 (d, 1H, J=2 Hz); 7.9-7.75 (m, 3H); 7.67 (m, 1H); 7.45 (m, 2H); 7.32 (d, 1H, J=2 Hz); 4.0 (m, 1H); 2.35 (s, 3H); 1.6 (d, 3H, J=7 Hz).

A solution of 1.5 g (4.8 mmol) of said acid in anhydrous toluene (10 mL), to which 2.1 mL of oxalyl chloride (24 mmol) were added, was heated to a temperature T=60° C. to disappearance of the starting acid (1.5 hours). After cooling to room temperature, the solvent was evaporated first under nitrogen flow and then in high-vacuum conditions to yield an oily yellow residue (1.55 g) of the chloride of the acid, which was used as such. To a solution of the compound in anhydrous toluene (15 mL) cooled to a temperature T=0° C., a solution of dimethylethyl amine (1.56 mL; 14.4 mmol) in a few mL of toluene was added dropwise, under stirring, in 3 hours. The reaction mixture was then cooled to a temperature T=−70° C., and a solution of R(−)-pantolactone (0.656 g; 5.04 mmol) in anhydrous toluene (2 mL) was finally added, dropwise, to said mixture. The temperature was then allowed to rise to −20° C., and the reaction mixture was kept under stirring at this temperature for a total of 18 hours. The residue, obtained after evaporation of the solvent at low pressure, was purified by means of column chromatography to yield 1.42 g (3.36 mmol) of dihydro-3-hydroxy-4,4-dimethyl-2(3H)-furanone R(−)-2-acetoxy-5-benzoylphenyl propionate in the form of a transparent oil and as sole diastereoisomer;

$^1$H-MR ($CDCl_3$): δ 8.2 (d, 1H, J=2 Hz); 7.9-7.7 (m, 4H); 7.32 (m, 2H); 7.32 (d, 1H, J=2 Hz); 4.15 (m, 1H); 4.01 (m, 3H); 2.35 (s, 3H); 1.6 (d, 3H, J=7 Hz); 1.25 (s, 3H); 1.05 (s, 3H).

To a solution of 1.4 g of the ester (3.3 mmol) in absolute ethyl alcohol (10 mL), cooled to a temperature T=0° C., was added a 0.37N aqueous solution of lithium hydroxide (31.2 mL; 11.55 mmol). This was kept under stirring at a temperature T=0° C. for 2 hours; then it was acidified to pH 5.5-6 by adding dropwise a 5% aqueous solution of citric acid, and finally extracted with ethyl acetate (3×15 mL). The organic extracts were combined and washed with water (20 mL), dried on Na$_2$SO$_4$, and evaporated at low pressure. The subsequent purification of the residual crude oil by means of flash chromatography (eluent CH2Cl2/CH3OH 95:100) yielded R(−)-2-(2-hydroxy-5-benzoylphenyl)-propionic acid in the form of a white solid (0.365 g; 1.35 mmol): m.p. 170-172° C.; [α]$_D$=−62 (c=1%; CH3OH);

$^1$H-NMR (CDCl$_3$): δ 9.5 (bs, COOH); 8.0 (d, 1H, J=2 Hz); 7.9-7.75 (m, 3H); 7.67 (m, 1H); 7.45 (m, 2H); 7.32 (d, 1H, J=2 Hz); 7.05 (s, OH); 4.0 (m, 1H); 1.6 (d, 3H, J=7 Hz). The subsequent esterification of the acid with acetic anhydride (0.2 g; 0.74 mmol) in anhydrous acetone (5 mL), in the presence of finely ground K$_2$CO$_3$ (0.25 g; 1.8 mmol) as bottom body, yielded R(−)-2-(2-acetoxy-5-benzoylphenyl)-propionic acid in the form of a colourless oil (0.17 g; 0.545 mmol): [α]$_D$=−53 (c=1; CH$_3$OH);

$^1$H-NMR (CDCl$_3$): δ 9.5 (bs, COOH); 8.0 (d, 1H, J=2 Hz); 7.9-7.75 (m, 3H); 7.67 (m, 1H); 7.45 (m, 2H); 7.32 (d, 1H, J=2 Hz); 4.5 (m, 1H); 2.37 (s, 3H); 1.6 (d, 3H, J=7 Hz).

17b—General Procedure for the Synthesis of 2-Arylpropionic Acids and Related R Enantiomers of Formula Vf (R3=H)

To a stirred solution of a 3-hydroxyacetophenone (80 mmol) (or alternatively 2- or 4-hydroxyacetophenone) in acetone (80 mL), dry K$_2$CO$_3$ (12.0 g; 86.2 mmol) is added at r.t. After stirring 30' at r.t. a solution of perfluorobutanesulfonyl fluoride (15.5 mL; 86.1 mmol) in acetone (30 mL) is dropped and the resulting mixture refluxed for 2 h. After cooling at r.t. the formed solid is filtered off and the filtrate is evaporated under vacuum to give a crude residue which is diluted with EtOAc (100 mL). The organic solution is stirred and washed with a saturated solution of K$_2$CO$_3$ (20 ml) and then with a saturated solution of NaCl (20 mL), dried over Na$_2$SO$_4$ and evaporated under vacuum to give in a quantitative yield the perfluorobutanesulfonyl ester as oil pure enough to be used in the next step.

A mixture of acetophenone perfluorobutanesulfonyl ester (80 mmol), elemental sulfur (2.95 g; 92 mmol) and morpholine (8.0 mL; 92 mmol) is refluxed for 6 h. After cooling at r.t. the mixture is carefully added to a stirred ice/6N HCl mixture (40 mL). After dilution with CH$_2$Cl$_2$ (50 mL), the two phases are stirred and separated and the aqueous one is extracted again with CH$_2$Cl$_2$ (2×50 mL). The collected organic extracts are dried over Na$_2$SO$_4$ and evaporated under vacuum; the resultant crude yellow oily residue, after purification by flash chromatography (n-hexane/EtOAc 9:1) gives the related morpholinthioamide as colourless oil (yield 73-80%).

To a solution of morpholinthioamide (58 mmol) and glacial acetic acid (25 mL), 37% HCl (40 mL) is carefully added and the solution is refluxed under stirring for 16 h. After cooling at r.t. the formed solid is filtered off and the filtrate, after evaporation, is diluted with water (50 mL). The aqueous phase is extracted with EtOAc (2×50 ML) and the collected organic extracts are washed back with a saturated solution of NaCl (20 mL), dried over Na$_2$SO$_4$ and evaporated under vacuum to give a crude residue which, by crystallisation from n-hexane, gives the (o,m,p,)-perfluorobutanesulfonate-2-phenylacetic acid as solid (yield 90-93%). The subsequent treatment with conc. H$_2$SO$_4$ in abs. EtOH at T=50° C. yields the corresponding ethyl ester in a quantitative yield.

A suspension of 60% NaH in mineral oil (1.6 g; 66.7 mmol) is added in small portions to an ice cooled and stirred solution of ethyl (o,m,p,)-perfluorobutanesulfonyloxy-2-phenyl acetate (25 mmol) in THF (50 mL). After 15' methyl iodide (1.88 mmol; 30.2 mmol) is dropped into the solution and the resulting dark solution is stirred for 3.5 h at r.t. After adding a saturated solution of NH$_4$Cl (45 mL) the organic solvent is evaporated under vacuum and the aqueous phase is extracted with CH$_2$Cl$_2$ (3×50 mL); the collected organic extracts are washed back with a saturated solution of NaCl (20 mL), dried over Na$_2$SO$_4$ and evaporated under vacuum to give a crude residue which, after chromatography, gives the corresponding 3-perfluorobutanesulfonyloxy-2-phenyl propionic acid as pale yellow oil (yield 70%).

Starting from ethyl (2- or 3- or 4)-perfluorobutanesulfonyloxy-2-phenyl propionate, racemic mixtures of 2-arylpropionic acids of general formula Aryl-C(CH$_3$)H—COOH (Va) have been synthesized according the reaction of the above mentioned perfluoroalkanesulfonates with several tributyltinalkyl, alkenyl or alkynyl compounds as described in Mitchell T. N., Synthesis, 803, 1992 and Ritter K., Synthesis, 735, 1993.

According the above method the following compounds have been prepared:

17b1. 2-[3'-isopropenyl phenyl]propionic acid

Ethyl 3'-perfluorobutanesulfonyloxy-2-phenyl propionate (7.63 mmol) is dissolved in N-methylpyrrolidone (30 mL) and treated with dry LiCl (0.94 g, 22.9 mmol), triphenylarsine (90 mg; 0.3 mmol) and dipalladiumtribenzylidenacetone (0.193 g; 0.15 mmol Pd). After 5' at r.t., tributylisopropenyltin (2.83 g; 8.55 mmol) is added and the solution stirred at T=90° C. for 5 h. After cooling solution with sat. aq. KF and n-hexane, filtration and separation of the organic phase is followed by drying over Na$_2$SO$_4$ and evaporation under vacuum. Purification of the crude residue by flash chromatography gives ethyl 2-[3'-isopropenyl phenyl]propionate (1.24 g; 5.3 mmol). Yield 70%

To a solution of the ester in dioxane (5 mL) 1N NaOH (5 mL) is added and the resulting solution is stirred overnight at r.t. After evaporation of the organic solvent the aqueous mixture is acidified at pH=2 with 2N HCl; the product is isolated by filtration as white solid (1.03 g; 5 mmol).

$^1$H-NMR (CDCl$_3$): δ 10.0 (bs, 1H, COO$\underline{H}$); 7.28 (m, 1H); 7.15 (m, 1H); 7.05 (m, 2H); 5.02 (s, 2H); 3.75 (m, 1H); 1.45 (d, 3H, J=7 Hz); 0.78 (s, 3H).

17b2. 3-[3'-(1"-styrenyl)phenyl]propionic acid

The acid has been synthesised by tributyl-(α-methyl styrenyl)propenyl tin as reagent prepared according the above method.

$^1$H-NMR (CDCl$_3$): δ 11.0 (bs, 1H, COO$\underline{H}$); 7.38-7.13 (m, 9H); 3.95 (m, 2H); 3.81 (m, 1H); 1.72 (d, 3H, J=7 Hz).

The above acids 17b1 and 17b2 have also been used as intermediates in the synthesis of acids 17b3 and 17b4.

17b3. 2-[3'-(isopropyl)phenyl]propionic acid

A mixture of ethyl 2-[3'-(isopropenyl)phenyl]propionate (1 g; 4.6 mmol), prepared according the above method, 95% EtOH and 10% Pd/C (100 mg) is hydrogenated at r.t. and atmospheric pressure until the starting material disappears (2 h). The catalyst is filtered off on Celite panel and, after evaporation under vacuum, the so obtained transparent oil (0.99 g; 4.5 mmol) is hydrolysed by 1N KOH in EtOH (10 mL) at T=80° C. for 2 h. After cooling at r.t. the solvent is evaporated under vacuum and the crude residue is diluted with EtOAc (20 mL); the organic phase is extracted with water (3×10 mL); the aqueous collected phases are acidified to pH=2 by 2N HCl and extracted back with EtOAc (2×10 mL); the organic collected extracts are washed with a saturated solution of NaCl, dried over $Na_2SO_4$ and evaporated under vacuum to give the desired acid (0.75 g; 3.6 mmol).

$^1$H-NMR (CDCl$_3$): δ 10.5 (bs, 1H, COO$\underline{H}$); 7.15-7.08 (m, 4H); 3.55 (m, 1H); 2.91 (m, 1H); 1.45 (d, 3H, J=7 Hz); 1.26 (d, 6H, J=7 Hz).

According the same method and starting from 3-[3'-(1"-styrenyl)phenyl]propionic acid the following compound has been prepared:

17b4. (R,S)2-[3'-(α-methyl benzyl)phenyl]propionic acid $^1$H-NMR (CDCl$_3$): δ 11.0 (bs, 1H, COO$\underline{H}$); 7.38-7.13 (m, 9H); 4.20 (m, 1H); 3.78 (m, 1H); 1.72 (d, 3H, J=7 Hz); 1.55 (d, 3H, J=7 Hz).

Each of the racemic mixtures of acids with general formula (Vf) is transformed in the sole R enantiomer through a stereospecific synthesis of the corresponding R-pantolactone esters (through a ketene intermediate) following the procedures cited in Myers A. G. et al., J. Am. Chem. Soc., 119, 6496, 1997 and in Larsen R. D. et al., J. Am. Chem. Soc., 111, 7650 1989, as described in Example 17a, In this way the following acids have been prepared:

17b5. (R)-2-[(3'-isopropyl)phenyl]propionic acid $[α]_D$=−23 (c=0.5; $CH_2Cl_2$)
$^1$H-NMR (CDCl$_3$): δ 10.0 (bs, 1H, COO$\underline{H}$); 7.15-7.10 (m, 4H); 3.65 (m, 1H); 2.90 (m, 1H); 1.45 (d, 3H, J=7 Hz); 1.32 (d, 6H, J=7 Hz).

17b6. (R),(R',S')2-[3'-(α-methyl benzyl)phenyl]propionic acid $[α]_D$=−49 (c=0.5; $CH_2Cl_2$)
$^1$H-NMR (CDCl$_3$): δ 11.0 (bs, 1H, COO$\underline{H}$); 7.38-7.13 (m, 9H); 4.20 (m, 1H); 3.78 (m, 1H); 1.72 (d, 3H, J=7 Hz); 1.55 (d, 3H, J=7 Hz).

17b7. (R)2-[2'-(2,6-dichlorophenylamino)phenyl]propionic acid

The preparation of (R,S)2-[2'-(2,6-dichlorophenylamino)phenyl]propionic acid has been performed according Geigy, J R; GB Patent 1,132,318 (Oct. 30, 1968). The subsequent optical resolution has been performed through salt formation with R(+)-N-methylbenzylamine according to the method in Akguen et al., Arzneim. Forsch. 1996, 46:9 891-894.

17b8. (R),(R',S')2-[3'-α-hydroxy benzyl)phenyl] propionic acid

To a solution of R(−)-ketoprofen (0.254 g; 1 mmol) in ethyl alcohol (5 mL), triethylamine (0.12 g; 1 mmol) and 5% Pd/C (0.025 g) are added; the mixture is then hydrogenated at r.t. and atmospheric pressure for 3 h.

After the catalyst has been filtered off on Celite panel the filtrate is evaporated and the crude residue is purified by flash chromatography to give the product as white powder (yield 85%).

$[α]_D$=−45.7 (c=1; CHCl$_3$)
$^1$H-NMR (CDCl$_3$): δ 7.41-7.3 (m, 3H); 7.31-7.14 (m, 6H); 5.75 (s, 1H); 4.02 (bs, 1H, O$\underline{H}$); 3.68 (q, J=7 Hz); 1.4 (d, 3H, J=7 Hz).

17b9. (R),(R',S')2-[3'-(α-hydroxy-α-methylbenzyl)phenyl]propionic acid

To a solution of R(−)-ketoprofen methyl ester (0.269 g; 1 mmol) in diethyl ether (10 mL) 3.0M in diethyl ether methylmagnesium bromide (2 mmol) is added and the resulting solution is refluxed for 2 h. After cooling at r.t. the organic phase is washed with a solution of 5% NaH$_2$PO$_4$ (2×10 mL), dried over Na$_2$SO$_4$ and evaporated under vacuum to give a crude residue which is dissolved in a 1:1 solution of 1N NaOH/MeOH (5 mL). After stirring overnight The solvent is evaporated under vacuum and the aqueous phase is acidified at pH=2; the formed precipitate is filtered and washed with water to give (R),(R',S')2-[3'-(α-hydroxy-α-methylbenzyl)phenyl]propionic acid as white powder.

$[α]_D$=−45.3 (c=1; CHCl$_3$)
$^1$H-NMR (CDCl$_3$): δ 7.41-7.3 (m, 3H); 7.31-7.14 (m, 6H); 4.02 (bs, 1H, O$\underline{H}$); 3.68 (q, J=7 Hz); 2.12 (s, 3H); 1.4 (d, 3H, J=7 Hz).

17b10. (R)-2-[(3'-α-hydroxy isopropyl)phenyl]propionic acid

Following the same procedure and starting from (R)-2-[(3'-acetyl)phenyl]propionic acid, obtained by optical resolution according the method above mentioned from its racemic mixture, the title compound is obtained as white powder (Yield 70%)

$^1$H-NMR (CDCl$_3$): δ 7.31-7.14 (m, 4H); 4.02 (bs, 1H, O$\underline{H}$); 3.68 (q, J=7 Hz); 1.85 (s, 6H); 1.4 (d, 3H, J=7 Hz).

Example 18

General Procedure for Preparation of Acyl Chlorides of 2-arylpropionic acids

A solution of R(−)-2-[(4'-isobutyl)phenyl]propionic acid (72.8 mmol) in thionyl chloride (37.5 mL) is refluxed for 3 h; after cooling at r.t. the solvent is evaporated under vacuum. The crude oily residue is used as it is for the next step.

IR (film) cm$^{-1}$: 1800 (ClC=O)

Example 19

19a. (R)-2-[(3'-isopropyl)phenyl]-N-(carboxymethyl)propionamide

To a cooled (T=0-5° C.) solution of (R)-2-[(3'-isopropyl)phenyl]propionic acid (4.75 g; 24.24 mmol) in DMF (20 mL) hydroxybenzotriazole (HOBT) (22.2 mmol) is added under stirring. After 15' a mixture of glycine methyl ester hydrochloride (2.89 g; 22.2 mmol) and triethylamine (3 mL) in DMF (5 mL) is added; at last N,N-dicyclohexylcarbodiimide (DCC), (24.24 mmol) is added portionwise. The resulting mixture is stirred for 2 h at T=0° C. and then overnight at r.t. After the formed precipitate is filtered off, the filtrate is diluted with EtOAc (50 mL): the organic phase is washed with 10% citric acid (2×20 mL), with a saturated solution of NaHCO$_3$ (2×20 mL) and with a saturated solution of NaCl (20 mL), dried over Na$_2$SO$_4$ and evaporated under vacuum to give a crude residue. After washing with n-hexane the pure ester is obtained as white solid (5.2 g; 19.4 mmol).

To a solution of the ester (5.2 g; 19.4 mmol) in dioxane (25 mL) 1N NaOH (25 mL) is added and the resulting solution is stirred overnight at r.t. After evaporation of the organic solvent the aqueous mixture is acidified at pH=2 with 2N HCl; the product is isolated by filtration as white solid (4.8 g; 19 mmol).

$[\alpha]_D=-53$ (c=1; CHCl$_3$)
$^1$H-NMR (CDCl$_3$): δ 10.00 (bs, 1H, COO<u>H</u>); 7.28 (m, 1H); 7.15 (m, 1H); 7.05 (m, 2H); 5.90 (bs, 1H, CON<u>H</u>); 4.12-3.90 (m, 2H); 3.75 (q, 1H, J=7 Hz); 2.34 (m, 1H); 1.45 (d, 3H, J=7 Hz); 0.78 (d, 6H, J=8 Hz).

According to the same procedure the following compounds have been synthesised:

19b. (R)(R',S')-2-[3'-(α-methylbenzyl)phenyl]-N-(carboxymethyl)propionamide $[\alpha]_D=-35$ (c=1; CHCl$_3$)
$^1$H-NMR (CDCl$_3$): δ 10.5 (bs, 1H, COO<u>H</u>); 7.38-7.13 (m, 9H); 5.85 (bs, 1H, CON<u>H</u>); 4.10-3.95 (m, 2H); 4.20 (m, 1H); 3.78 (m, 1H); 1.72 (d, 3H, J=7 Hz); 1.55 (d, 3H, J=7 Hz).

19c. (R),(R',S')2-[3'-(α-hydroxybenzyl)phenyl]-N-(carboxymethyl)propionamide $[\alpha]_D=-39.1$ (c=1; CHCl$_3$)
$^1$H-NMR (CDCl$_3$): δ 10.05 (bs, 1H, COO<u>H</u>); 7.41-7.3 (m, 3H); 7.31-7.14 (m, 6H); 5.92 (bs, 1H, CON<u>H</u>); 5.75 (s, 1H); 4.45 (bs, 1H, O<u>H</u>); 4.12-3.90 (m, 2H); 3.68 (q, J=7 Hz); 1.4 (d, 3H, J=7 Hz).

19d. (R),(R' S')2-[3'-(α-hydroxy-α-methylbenzyl)phenyl]-N-(carboxymethyl)propionamide $[\alpha]_D=-41$ (c=1; CHCl$_3$)
$^1$H-NMR (CDCl$_3$): δ 9.92 (bs, 1H, COO<u>H</u>); 7.40-7.28 (m, 3H); 7.25-7.10 (m, 6H); 5.85 (bs, 1H, CON<u>H</u>); 4.45 (bs, 1H, O<u>H</u>); 4.10-3.95 (m, 2H); 3.68 (q, J=7 Hz); 2.15 (s, 3H); 1.4 (d, 3H, J=7 Hz).

Example 20

R(−)—N-methoxy-2-(4'-isobutyl)phenyl propionamide

To a solution of 2-(4'-isobutylphenyl)propionyl chloride (1 g; 4.34 mmol) in dry CH$_2$Cl$_2$ (20 mL) O-methylhydroxylamine hydrochloride (0.435 g; 5.201 mmol) and triethylamine (1.44 mL; 10.41 mmol) are added. The resulting mixture is stirred at r.t. overnight. The organic phase is washed with 4N HCl (2×10 mL), dried over Na$_2$SO$_4$ and evaporated under vacuum to give the pure product as a pale yellow oil (1 g; 4.2 mmol).

$[\alpha]_D=-34$ (c=1; EtOH)
$^1$H-NMR (CDCl$_3$): δ 7.8 (bs, 1H, CON<u>H</u>); 7.05 (d, 2H, J=8 Hz); 6.95 (d, 2H, J=8 Hz); 3.51 (bs, 3H); 3.45 (m, 1H); 2.32 (d, 2H, J=7 Hz); 1.82 (m, 1H); 1.45 (t, 3H, J=7 Hz); 0.82 (d, 6H, J=7 Hz).

Example 21

R(−)-2-[(4'-isobutyl)phenyl]-N-(carboxymethoxyl)propionamide

To a cooled (T=0-5° C.) solution of (R)-2-[(4'-isobutyl)phenyl]propionic acid (5 g; 24.24 mmol) in DMF (20 mL) hydroxybenzotriazole (HOBT) (22.2 mmol) is added under stirring. After 15' a mixture of carboxymethoxylamine hemihydrochloride (2.65 g; 12.12 mmol) and triethylamine (3 mL) in DMF (5 mL) is added; at last N,N-dicyclohexylcarbodiimide (DCC) (24.24 mmol) is added portionwise. The resulting mixture is stirred for 2 h at T=0° C. and then overnight at r.t. After the formed precipitate is filtered off, the filtrate is diluted with n-hexane (50 mL); the formed precipitate is filtered and purified by flash chromatography on silica gel to give the desired product as white powder (1.69 g; 6 mmol).

$[\alpha]_D=-17.6$ (c=0.6; CH$_3$OH)
$^1$H-NMR (CDCl$_3$): δ 9.3 (bs, 2H, CON<u>H</u>+COO<u>H</u>); 7.05 (d, 2H, J=8 Hz); 6.95 (d, 2H, J=8 Hz); 4.35 (s, 2H); 3.45 (m, 1H); 2.34 (d, 2H, J=7 Hz); 1.85 (m, 1H); 1.45 (d, 3H, J=7 Hz); 0.81 (d, 6H, J=7 Hz).

Example 22

R(−)-2-[(2',6'-dichlorophenyl)amino]-phenyl-N-(2''-hydroxy-2'''-ethoxyethyl)propionamide To a cooled (T=0-5° C.) solution of (R)2-[2'-(2,6-dichlorophenylamino)phenyl]propionic acid (7.51 g; 24.24 mmol) in DMF (20 mL) hydroxybenzotriazole HOBT (22.2 mmol) is added under stirring. After 15' 2-aminoethoxyethanol (2.33 g; 22.2 mmol) in DMF (5 mL) is added; at last N,N-dicyclohexylcarbodiimide (DCC) (24.24 mmol) is added portionwise. The resulting mixture is stirred for 2 h at T=0° C. and then overnight at r.t. After the formed precipitate is filtered off, the filtrate is evaporated under vacuum; the crude residue is purified by flash chromatography to give R(−)-2-[(2',6'-dichlorophenyl)amino]-phenyl-N-(2''-hydroxy-2'''-ethoxyethyl)propionamide as a white solid (6.44 g; 16.7 mmol).

$[\alpha]_D=-51$ (c=1; EtOH)
$^1$H-NMR (CDCl$_3$): δ 7.35 (d, 2H, J=8 Hz); 7.20-7.05 (m, 2H); 7.00-6.85 (m, 2H); 6.55 (d, 1H, J=8 Hz); 6.18 (bs, 1H, CON<u>H</u>); 3.85 (m, 1H); 3.65-3.40 (m, 8H); 1.45 (d, 3H, J=7 Hz).

Example 23

R(−)-2-[(3'-acetyl)phenyl]-N-(4''-pyrimidyl)propionamide

A solution of R(−)-2-[(3'-acetyl)phenyl]propionyl chloride (0.96 g; 4.27 mmol) in dry CH$_2$Cl$_2$ (10 mL) is added dropwise to a solution of 4-aminopyrimidine (1 g; 10 mmol) in dry CH$_2$Cl$_2$ (10 mL). The resulting solution is stirred at r.t. overnight. The formed precipitate is filtered off and the filtrate is washed with water (2×10 mL), a saturated solution of NaCl, dried over Na$_2$SO$_4$ and evaporated under vacuum to give a crude residue purified by crystallisation from n-hexane. The pure product is obtained as a white solid (0.62 g; 2.3 mmol).

$[\alpha]_D=-139$ (c=0.5; CH$_3$OH)
$^1$H-NMR (CDCl$_3$): δ 8.80 (s, 1H); 8.60 (m, 1H); 8.20 (d, 1H, J=4 Hz); 8.00-7.95 (m, 2H); 7.81 (bs, 1H, CON<u>H</u>); 7.63 (d, 1H, J=7 Hz); 7.42 (t, 1H, J=7 Hz); 3.80 (q, 1H, J=7 Hz); 2.6 (s, 3H); 1.54 (d, 3H, J=7 Hz).

Example 24

(R)-2-[(3'α-hydroxy isopropyl)phenyl]-N-(methoxyethyl)propionamide

To a cooled (T=0-5° C.) solution of (R)-2-[(3'-α-hydroxy isopropyl)phenyl]propionic acid (5.04 g; 24.24 mmol) in DMF (20 mL) hydroxybenzotriazole (HOBT) (22.2 mmol) is added under stirring. After 15' O-methylethanolamine (1.66 g; 22.2 mmol) in DMF (5 mL) is added; at last N,N-dicyclohexylcarbodiimide (DCC) (24.24 mmol) is added portionwise. The resulting mixture is stirred for 2 h at T=0° C. and then overnight at r.t. After the formed precipitate is filtered off, the filtrate is evaporated under vacuum; the crude residue is purified by flash chromatography to give (R)-2-[(3'-α-hydroxy isopropyl)phenyl]-N-(methoxyethyl)propionamide as a colourless oil (5.3 g; 20 mmol).

$[\alpha]_D = -63$ (c=0.5; $CH_3OH$)

$^1$H-NMR ($CDCl_3$): δ 7.65 (bs, 1H, CON$\underline{H}$); 7.31-7.14 (m, 4H); 4.02 (bs, 1H, O$\underline{H}$); 3.78 (t, 2H, J=8 Hz); 3.68 (q, J=7 Hz); 3.4 (t, 2H, J=8 Hz); 3.1 (s, 3H); 1.85 (s, 6H); 1.4 (d, 3H, J=7 Hz).

The invention claimed is:

1. A method for the treatment of psoriasis, ulcerative cholitis, glomerular nephritis, acute respiratory insufficiency, idiopathic fibrosis, and rheumatoid arthritis in a mammal, comprising administering to a mammal in need thereof, a therapeutically effective amount of a compound of an isolated (R)-enantiomer of a 2-aryl-propionic amide of formula (I)

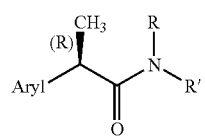

(I)

and pharmaceutically acceptable salts thereof,
wherein:
Aryl represents a substituted or unsubstituted aryl group;
R represents H, $C_1$-$C_4$-alkyl, allyl, propargyl, $CH_2$—$CO_2H$ or $(CH_2)_2$—$CO_2H$;
R' is:
  straight or branched $C_1$-$C_6$-alkyl, alkenyl, cycloalkyl, or phenylalkyl substituted with one or more carboxy groups $CO_2H$;
  straight or branched $C_1$-$C_6$-alkyl, alkenyl, cycloalkyl, or phenylalkyl substituted with one or more carboxy groups $CO_2H$ and with a heteroatom selected from oxygen or sulphur;
  a residue of formula —$CH_2$—$CH_2$—X—($CH_2$—$CH_2O)_n$R wherein R is hereinbefore defined, n being an integer from 0 to 5, whilst X is oxygen or sulphur;
  a residue of formula (R) or (S)—$CH(CH_3)CH_2$—O—$CH_2$—$CH_2$—OH;
  a residue of formula OR, wherein R is hereinbefore defined;
  a residue of formula (III)

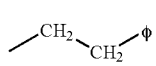

(III)

wherein
Φ represents 2-(1-methyl-pyrrolidyl), 2-pyridyl, 4-pyridyl, 1-imidazolyl, 4-imidazolyl, 1-methyl-4-imidazolyl, 1-methyl-5-imidazolyl or a NRaRb group wherein each Ra and Rb, which may be the same or different, represent $C_1$-$C_6$ alkyl or —$(CH_2)_m$—OH hydroxyalkyl wherein m is an integer from 2 to 3, and, alternatively, Ra and Rb together with the atom of N to which they are bound, constitute a heterocycle from 3 to 7 members of formula (IV)

(IV)

wherein
Y represents a single bond, $CH_2$, O, S or N-Rc, Rc being H, $C_1$-$C_6$ alkyl, $(CH_2)_m$—OH hydroxyalkyl, a —$(CH_2)_m$—Ar' residue wherein Ar' is an aryl, heteroaryl, cycloaliphatic and/or heterocycloaliphatic residue, m' is zero or an integer from 1 to 3, p and q, each independently, is an integer from 1 to 3; or
a heteroaryl selected from the group consisting of, 2-pyridyl or 4-pyridyl, 2-pyrimidinyl or 4-pyrimidinyl; 2-pyrazinyl, 5-methyl-2-pyrazinyl; 3-1,2,4-thiazinyl 3-1,2,4-thiazolyl, 3-1-benzyl-1,2,4-thiazolyl 2-1,3-thiazolidinyl, 2-1,3-thiazolyl, 1,3-oxazolyl, 3-isoxazolyl, 4-dihydro-3-oxo-isoxazolyl, 5-methyl-isoxazol-4-yl, 2-imidazolyl, 4-imidazolyl-5-carboxyamide and 2-imidazolyl-4,5-dicarbonitrile, 5-indanyl, 5-indazolyl, 7-aza-indol-3-yl, 2- or 3- or 4-quinolinyl;
wherein the compounds of formula I inhibit the chemotaxis of neutrophils induced by interleukin-8.

2. A method for the inhibition and the treatment of damages caused by ischaemia and reperfusion in a mammal comprising, administering to a mammal in need thereof, a therapeutically effective amount of an isolated (R)-enantiomer of a 2-aryl-propionic amide of formula (I)

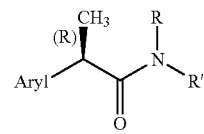

(I)

and pharmaceutically acceptable salts thereof,
wherein:
Aryl represents a substituted or unsubstituted aryl group;
R represents H, $C_1$-$C_4$-alkyl, allyl, propargyl, $CH_2$—$CO_2H$ or $(CH_2)_2$—$CO_2H$;
R' is:
  straight or branched $C_1$-$C_6$-alkyl, alkenyl, cycloalkyl, or phenylalkyl substituted with one or more carboxy groups $CO_2H$;
  straight or branched $C_1$-$C_6$-alkyl, alkenyl, cycloalkyl, or phenylalkyl substituted with one or more carboxy groups $CO_2H$ and with a heteroatom selected from oxygen or sulphur;
  a residue of formula —$CH_2$—$CH_2$—X—($CH_2$—$CH_2O)_n$R wherein R is hereinbefore defined, n being an integer from 0 to 5, whilst X is oxygen or sulphur;
  a residue of formula (R) or (S)—$CH(CH_3)CH_2$—O—$CH_2$—$CH_2$—OH;
  a residue of formula OR, wherein R is hereinbefore defined;
  a residue of formula (III)

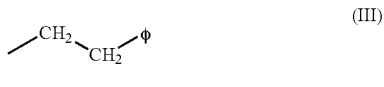
(III)

wherein

Φ represents 2-(1-methyl-pyrrolidyl), 2-pyridyl, 4-pyridyl, 1-imidazolyl, 4-imidazolyl, 1-methyl-4-imidazolyl, 1-methyl-5-imidazolyl or a NRaRb group wherein each Ra and Rb, which may be the same or different, represent $C_1$-$C_6$ alkyl or —$(CH_2)_m$—OH hydroxyalkyl wherein m is an integer from 2 to 3, and, alternatively, Ra and Rb together with the atom of N to which they are bound, constitute a hetero cycle from 3 to 7 members of formula (IV)

(IV)

wherein

Y represents a single bond, $CH_2$, O, S or N—$R^c$, Rc being H, $C_1$-$C_6$ alkyl, $(CH_2)_m$—OH hydroxyalkyl, a —$(CH_2)_m$—Ar' residue wherein Ar' is an aryl, heteroaryl, cycloaliphatic and/or heterocycloaliphatic residue, m' is zero or an integer from 1 to 3, p and g, each independently, is an integer from 1 to 3: or a heteroaryl selected from the group consisting of, 2-pyridyl or 4-pyridyl, 2-pyrimidinyl or 4-pyrimidinyl: 2-pyrazinyl, 5-methyl-2-pyrazinyl 3-1,2,4-thiazinyl 3-1,2,4-thiazolyl, 3-1-benzyl-1,2,4-thiazolyl 2-1,3-thiazolidinyl, 2-1,3-thiazolyl, 1,3-oxazolyl, 3-isoxazolyl, 4-dihydro-3-oxo-isoxazolyl, 5-methyl-isoxazol-4-yl, 2-imidazolyl, 4-imidazolyl-5-carboxyamide and 2-imidazolyl-4,5-dicarbonitrile, 5-indanyl, 5-indazolyl, 7-aza-indol-3-yl, 2- or 3- or 4-quinolinyl:

wherein the compounds of formula I inhibit the chemotaxis of neutrophils induced by interleukin-8.

3. The method of claim 1 wherein:

Aryl represents a substituted or unsubstituted aryl group;

R represents H, $C_1$-$C_4$-alkyl, allyl, propargyl, $CH_2$—$CO_2H$ or $(CH_2)_2CO_2H$; and R' is an (L) amino acid.

4. The method of claim 1 wherein:

Aryl represents a substituted or unsubstituted aryl group;

R represents H, $C_1$-$C_4$-alkyl, allyl, propargyl, $CH_2$—$CO_2H$ or $(CH_2)_2$—$CO_2H$; and R' is a residue of an L-amino acid selected from the group consisting of alanine, valine, leucine, isoleucine, norleucine, phenylalanine, tyrosine, histidine, S-methylcysteine, S-carboxymethylcysteine, S-2-hydroxyethylcysteine, methionine, O-methylserine, O-2-hydroxyethylserine, or a residue of glycine, phenylglycine, β-alanine, γ-amino-butyric acid, δ-amino-valeric acid, cis-4-amino-cyclohexancarboxylic acid, trans-4-aminomethyl-cyclohexancarboxylic acid, 3-amino-1,5-pentandioic acid, or a residue of formula (II),

(II)

wherein the A substituent represents H, straight or branched $C_1$-$C_6$-alkyl, $(CH_2)_mCO_2H$ wherein n is an integer between 1 and 3, benzyl, p-hydroxy-benzyl, —$CH_2$—O—$C_2H_5$, —$CH_2$—S—$CH_3$, —$CH_2$—S—$CH_2$—$CO_2H$, wherein the residues of the acids indicated above are in the form of a free acid or of a salt.

5. The method of claim 1 wherein:

Aryl represents a substituted or unsubstituted aryl group; and wherein R is hydrogen; and R' is the residue of L-alanine, L-carboxymethylcysteine, L-phenylalanine, L-leucine, L-methionine, L-O-methylserine, L-alanyl-glycine.

6. The method of claim 1 wherein the compound of formula (I) is selected from the group consisting of:

(R)(−)-2-(4'-isobutyl-phenyl)-N-methylpropionamide;

(R)(−)-2-[4'-isobutyl)phenyl]-N-carboxymethyl propionamide;

cis-(R)-2-[(4'-isobutyl)phenyl]-N-(4'carboxy-cyclohexyl) propionamide;

trans-(R)-2-[(4'-isobutyl)phenyl]-N-(4'carboxymethyl-cyclohexyl)propionamide;

(R,S')-2-[(4'-isobutyl)phenyl]-N-(2-carboxyethyl)propionamide;

(R,S')-2-[(4]-methoxy)phenyl]-N-(2-carboxyethyl)propionamide;

(R)—N-[2'-(4''-isobutylphenyl)propanoyl]-2-amino acrylic acid;

(R)(−)-2-[(4'-isobutyl)phenyl]-N-(2''-hydroxyethoxyethyl)propionamide;

(R,S')-2-[(4'-isobutyl)phenyl]-N-[1'methyl-2'-(2''''-hydroxyethoxy)ethyl]propionamide;

(R,R')-2-[(4'-isobutyl)phenyl]-N-[1'-methyl-2'-(2''''-hydroxyethoxy)ethyl]propionamide;

(R)(−)-2-(4'-isobutyl-phenyl)-N-(2''-pyridyl)propionamide and its hydrochloride;

(R)(−)-2-(4'-isobutyl-phenyl)-N-(4''-pyridyl)propionamide and its hydrochloride;

(R)(−)-2-[(3'-benzoyl)phenyl]-N-(2''-pyridyl)propionamide and its hydrochloride;

(R)(−)-2-[(2'-hydroxy-5'-benzoyl)phenyl]-N-(2''-pyridyl) propionamide and its hydrochloride;

(R)(−)-2-[(2'-hydroxy-5'-benzoyl)phenyl]-N-(4''-pyridyl) propionamide and its hydrochloride;

(R)(−)-2-[(2'-hydroxy-5'-benzoyl)phenyl]-N-carboxymethyl propionamide;

(R)(−)-2-(4'-isobutyl-phenyl)-N-(2''-pyrazinyl)propionamide and its hydrochloride;

(R)(−)-2-(4'-isobutyl-phenyl)-N-(2''-pyrimidinyl)propionamide and its hydrochloride;

(R)(−)-2-(4'-isobutyl-phenyl)-N-(4''-pyrimidinyl)propionamide and its hydrochloride;

(R)(−)-2-[(3'-isopropyl)phenyl]-N-carboxymethyl propionamide;

(R,S')(−)-2-[(3'-α-methylbenzyl)phenyl]-N-carboxymethyl propionamide; and (R,R')(−)-2-[(3'-α-methylbenzyl)phenyl]-N-carboxymethyl propionamide.

7. The method of claim 2 wherein:
Aryl represents a substituted or unsubstituted aryl group
R represents H, $C_1$-$C_4$-alkyl, allyl, propargyl, $CH_2$—$CO_2H$ or $(CH_2)_2$—$CO_2H$; and
R' is an (L) amino acid.

8. The method of claim 2 wherein:
Aryl represents a substituted or unsubstituted aryl group;
R represents H, $C_1$-$C_4$-alkyl, allyl, propargyl, $CH_2$—$CO_2H$ or $(CH_2)_2$—$CO_2H$; and
R' is an L-amino acid selected from the group consisting of alanine, valine, leucine, isoleucine, nor-leucine, phenylalanine, tyrosine, histidine, S-methylcysteine, S-carboxymethylcysteine, S-2-hydroxyethylcysteine, methionine, O-methylserine, O-2-hydroxyethylserine, or a residue of glycine, phenylglycine, β-alanine, γ-amino-butyric acid, δ-amino-valeric acid, cis-4-amino-cyclohexancarboxylic acid, trans-4-aminomethyl-cyclohexancarboxylic acid, 3-amino-1,5-pentandioic acid, or a residue of formula (II),

(II)

wherein the A substituent represents H, straight or branched $C_1$-$C_6$-alkyl, $(CH_2)_m CO_2H$ wherein n is an integer between 1 and 3, benzyl, p-hydroxy-benzyl, —$CH_2$—O—$C_2H_5$, —$CH_2$—S—$CH_3$, —$CH_2$—S—$CH_2$—$CO_2H$, wherein the residues of the acids indicated above are in the form of a free acid or of a salt or in the form of methyl, ethyl and allyl esters thereof.

9. The method of claim 2 wherein:
Aryl represents a substituted or unsubstituted aryl group;
R is hydrogen; and
R' is the residue of L-alanine, L-carboxymethylcysteine, L-phenylalanine, L-leucine, L-methionine, L-O-methylserine, L-alanyl-glycine.

10. The method of claim 2 wherein the compound of Formula (I) is selected from the group consisting of:
(R)(-)-2-(4'-isobutyl-phenyl)-N-methylpropionamide;
(R)(-)-2-[(4'-isobutyl)phenyl]-N-carboxymethyl propionamide;
cis-(R)-2-[(4'-isobutyl)phenyl]-N-(4'carboxy-cyclohexyl) propionamide;
trans-(R)-2-[(4'-isobutyl)phenyl]-N-(4'-carboxymethyl-cyclohexyl)propionamide;
(R,S')-2-[(4'-isobutyl)phenyl]-N-(2-carboxyethyl)propionamide;
(R, S')-2-[(4]-methoxy)phenyl]-N-(2-carboxyethyl)propionamide;
(R)—N-[2'-(4"-isobutylphenyl)propanoyl]-2-amino acrylic acid;
(R)(-)-2-[(4'-isobutyl)phenyl]-N-(2"-hydroxyethoxyethyl)propionamide;
(R,S")-2-[(4"-isobutyl)phenyl]-N-[1'methyl-2'-(2""-hydroxyethoxy)ethyl]propionamide;
(R,R')-2-[(4"-isobutyl)phenyl]-N-[1'-methyl-2'-(2""-hydroxyethoxy)ethyl]propionamide;
(R)(-)-2-(4'-isobutyl-phenyl)-N-(2"-pyridyl)propionamide and its hydrochloride;
(R)(-)-2-(4'-isobutyl-phenyl)-N-(4"-pyridyl)propionamide and its hydrochloride;
(R)(-)-2-[(3'-benzoyl)phenyl]-N-(2"-pyridyl)propionamide and its hydrochloride;
(R)(-)-2-[(2'-hydroxy-5'-benzoyl)phenyl]-N-(2"-pyridyl) propionamide and its hydrochloride;
(R)(-)-2-[(2'-hydroxy-5'-benzoyl)phenyl]-N-(4"-pyridyl) propionamide and its hydrochloride;
(R)(-)-2-[(2'-hydroxy-5'-benzoyl)phenyl]-N-carboxymethyl propionamide;
(R)(-)-2-(4'-isobutyl-phenyl)-N-(2"-pyrazinyl)propionamide and its hydrochloride;
(R)(-)-2-(4'-isobutyl-phenyl)-N-(2"-pyrimidinyl)propionamide and its hydrochloride;
(R)(-)-2-(4'-isobutyl-phenyl)-N-(4"-pyrimidinyl)propionamide and its hydrochloride;
(R)(-)-2-[(3'-isopropyl)phenyl]-N-carboxymethyl propionamide;
(R,S')(-)-2-[(3'-α-methylbenzyl)phenyl]-N-carboxymethyl propionamide; and
(R,R')(-)-2-[(3'-α-methylbenzyl)phenyl]-N-carboxymethyl propionamide.

11. The method of claim 1 wherein:
Aryl represents a substituted or unsubstituted aryl group;
R represents H, and
R' represents H, —CH2-CH3, L-CH2-(CH3)-CO2H, (CH2-CH2O)2H, 2-pyridyl or 4-pyridyl.

12. The method of claim 2 wherein:
Aryl represents a substituted or unsubstituted aryl group;
R represents H, and
R' represents H, —CH2-CH3, L-CH2-(CH3)-CO2H, (CH2-CH2O)2H, 2-pyridyl or 4-pyridyl.

13. The method of claim 2, wherein Aryl represents a phenyl group substituted with a group selected from isopropyl, acetyl, (2",6"-dichlorophenyl)amino, α-hydroxyisopropyl, (R,S) α-hydroxyethyl and its single R and S isomers, (R,S)-α-hydroxybenzyl and its single R and S isomers, and (R,S)-α-methylbenzyl and its single R and S isomers; (R,S)-α-hydroxy-α-methylbenzyl and its single R and S isomers.

14. The method of claim 2, wherein Aryl is selected from phenyl, 4-methyl-phenyl, 3-isopropyl-phenyl, 4-methoxyphenyl, 4-acetoxy-phenyl, 4-benzoyloxyphenyl, 4-hydroxyphenyl, 4-isobutylphenyl, 4-(2,2-dimethyl)vinylphenyl, $(CH_3)_2C$=CH—$C_6H_4$—, 4-(2-methyl)-allyl-phenyl, 3-benzoyl-phenyl, 3-phenoxy-phenyl, 3-benzyl-phenyl, 3-$C_6H_5$—CH(OH)-phenyl, 5-benzoyl-thien-2-yl, 4-thienoyl-phenyl, 1-oxo-2-isoindolinyl-phenyl, 2-fluoro-4-biphenylyl, 6-methoxynaphthyl, 5-benzoyl-2-acetoxy-phenyl, 5-benzoyl-2-hydroxy-phenyl, 3-α-methylbenzyl-phenyl, 3-hydroxypropylphenyl, 3-hydroxyethyl-phenyl.

15. The method of claim 1, wherein Aryl represents a phenyl group substituted with a group selected from isopropyl, acetyl, (2",6"-dichlorophenyl)amino, α-hydroxyisopropyl, (R,S) α-hydroxyethyl and its single R and S isomers, (R,S)-α-hydroxybenzyl and its single R and S isomers, and (R,S)-α-methylbenzyl and its single R and S isomers; (R,S)-α-hydroxy-α-methylbenzyl and its single R and S isomers.

16. The method of claim 1, wherein Aryl is selected from phenyl, 4-methyl-phenyl, 3-isopropyl-phenyl, 4-methoxyphenyl, 4-acetoxy-phenyl, 4-benzoyloxyphenyl, 4-hydroxyphenyl, 4-isobutylphenyl, 4-(2,2-dimethyl)vinylphenyl, $(CH_3)_2C$=CH—$C_6H_4$—, 4-(2-methyl)-allyl-phenyl, 3-benzoyl-phenyl, 3-phenoxy-phenyl, 3-benzyl-phenyl, 3-$C_6H_5$—CH(OH)-phenyl, 5-benzoyl-thien-2-yl, 4-thienoyl-phenyl, 1-oxo-2-isoindolinyl-phenyl, 2-fluoro-4-biphenylyl, 6-methoxynaphthyl, 5-benzoyl-2-acetoxy-phenyl, 5-benzoyl-2-hydroxy-phenyl, 3-α-methylbenzyl-phenyl, 3-hydroxypropylphenyl, 3-hydroxyethyl-phenyl.

* * * * *

UNITED STATES PATENT AND TRADEMARK OFFICE
CERTIFICATE OF CORRECTION

| | | |
|---|---|---|
| PATENT NO. | : 7,705,050 B2 | Page 1 of 1 |
| APPLICATION NO. | : 10/203463 | |
| DATED | : April 27, 2010 | |
| INVENTOR(S) | : Allegretti et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 60 days.

Signed and Sealed this

Twenty-second Day of February, 2011

David J. Kappos
*Director of the United States Patent and Trademark Office*